US012121299B2

(12) United States Patent
Brown

(10) Patent No.: US 12,121,299 B2
(45) Date of Patent: Oct. 22, 2024

(54) THERMAL COOLING RING FOR RADIATION THERAPY SYSTEM

(71) Applicant: RefleXion Medical, Inc., Hayward, CA (US)

(72) Inventor: Christopher Eric Brown, Morgan Hill, CA (US)

(73) Assignee: RefleXion Medical, Inc., Hayward, CA (US)

( * ) Notice: Subject to any disclaimer, the term of this patent is extended or adjusted under 35 U.S.C. 154(b) by 548 days.

(21) Appl. No.: 17/313,736

(22) Filed: May 6, 2021

(65) Prior Publication Data

US 2021/0267683 A1 Sep. 2, 2021

Related U.S. Application Data

(63) Continuation of application No. PCT/US2019/061180, filed on Nov. 13, 2019.

(60) Provisional application No. 62/769,269, filed on Nov. 19, 2018.

(51) Int. Cl.
| | | |
|---|---|---|
| *A61B 6/00* | (2024.01) | |
| *A61B 18/20* | (2006.01) | |
| *A61N 5/06* | (2006.01) | |
| *A61N 5/00* | (2006.01) | |

(52) U.S. Cl.
CPC .......... *A61B 18/203* (2013.01); *A61N 5/0616* (2013.01); *A61N 2005/005* (2013.01); *A61N 2005/0632* (2013.01)

(58) Field of Classification Search
CPC ....... A61B 18/20; A61B 18/203; A61B 6/037; A61B 6/4488; A61B 6/032; A61B 6/0407; A61B 6/4435; A61N 5/06; A61N 5/0616; A61N 5/1081; A61N 2005/005; A61N 2005/0632; A61N 2005/1052; A61N 2005/1061
See application file for complete search history.

(56) References Cited

U.S. PATENT DOCUMENTS

| | | | |
|---|---|---|---|
| 3,767,883 | A | 10/1973 | Staats |
| 3,773,106 | A | 11/1973 | Levy |
| 3,794,840 | A | 2/1974 | Scott |
| 3,844,341 | A | 10/1974 | Bimshas, Jr. et al. |

(Continued)

FOREIGN PATENT DOCUMENTS

| | | |
|---|---|---|
| CN | 1799509 A | 7/2006 |
| CN | 101297759 A | 11/2008 |

(Continued)

OTHER PUBLICATIONS

Extended European Search Report mailed on Jun. 9, 2020, for EP Application No. 17 871 349.1, filed on Nov. 15, 2017, 6 pages.

(Continued)

*Primary Examiner* — Jurie Yun
(74) *Attorney, Agent, or Firm* — Cooley LLP

(57) ABSTRACT

In some embodiments, an apparatus comprises a stationary frame and a thermal ring. The thermal ring may be rotatably coupled to the stationary frame and disposed relative to the stationary frame such that the thermal ring and the stationary frame define an enclosure. The thermal ring may include a thermally-conductive substrate configured to be in thermal contact with a heat-generating component. Heat from the heat-generating component may be transferred to the stationary frame via the enclosure.

18 Claims, 9 Drawing Sheets

(56) References Cited

U.S. PATENT DOCUMENTS

| | | |
|---|---|---|
| 5,299,249 A | 3/1994 | Burke et al. |
| 5,577,026 A | 11/1996 | Gordon et al. |
| 6,115,454 A | 9/2000 | Andrews et al. |
| 6,137,114 A | 10/2000 | Rohe et al. |
| 10,695,586 B2 | 6/2020 | Harper et al. |
| 2004/0030246 A1 | 2/2004 | Townsend et al. |
| 2005/0197564 A1 | 9/2005 | Dempsey |
| 2006/0113482 A1 | 6/2006 | Pelizzari et al. |
| 2008/0043910 A1 | 2/2008 | Thomas |
| 2009/0256078 A1 | 10/2009 | Mazin |
| 2010/0040197 A1 | 2/2010 | Maniawski et al. |
| 2011/0210261 A1 | 9/2011 | Maurer, Jr. |
| 2012/0035470 A1 | 2/2012 | Kuduvalli et al. |
| 2012/0213334 A1 | 8/2012 | Dirauf et al. |
| 2015/0126801 A1 | 5/2015 | Matteo et al. |
| 2015/0190658 A1 | 7/2015 | Yu |
| 2020/0368557 A1 | 11/2020 | Harper et al. |

FOREIGN PATENT DOCUMENTS

| | | |
|---|---|---|
| CN | 101378805 A | 3/2009 |
| CN | 103071241 A | 5/2013 |
| CN | 103650095 A | 3/2014 |
| CN | 105073188 A | 11/2015 |
| DE | 10-2013-205606 A1 | 10/2014 |
| EP | 0 437 434 B1 | 7/1995 |
| EP | 0 817 978 B1 | 8/2001 |
| EP | 1 762 177 A2 | 3/2007 |
| EP | 2 872 913 B1 | 2/2016 |
| FR | 2839894 A1 | 11/2003 |
| GB | 9520564 | 12/1995 |
| GB | 69634119 T2 | 2/2006 |
| GB | 201307806 | 6/2013 |
| GB | 2513596 A | 11/2014 |
| JP | H-01-156830 A | 6/1989 |
| JP | H-09-122110 A | 5/1997 |
| JP | 2002-263090 A | 9/2002 |
| JP | 2008-173184 A | 7/2008 |
| JP | 2010-500910 A | 1/2010 |
| JP | 2013-545560 A | 12/2013 |
| JP | 2014-521370 A | 8/2014 |
| NL | 9520013 A | 2/1997 |
| WO | WO-2009/114117 A2 | 9/2009 |
| WO | WO-2009/114117 A3 | 9/2009 |
| WO | WO-2010/109585 A1 | 9/2010 |
| WO | WO-2012/135771 A1 | 10/2012 |
| WO | WO-2015/038832 A1 | 3/2015 |
| WO | WO-2015/103564 A1 | 7/2015 |
| WO | WO-2015/134953 A1 | 9/2015 |
| WO | WO-2015/161036 A1 | 10/2015 |
| WO | WO-2017/220116 A1 | 12/2017 |
| WO | WO-2020/208207 A1 | 10/2020 |

OTHER PUBLICATIONS

Extended European Search Report mailed on Mar. 30, 2022, for EP Application No. 21 195 331.0, filed on Nov. 15, 2017, 11 pages.
Fan, Q. et al. (2012). "Emission Guided Radiation Therapy for Lung and Prostrate Cancers: A Feasibility Study on a Digital Patient," *Med. Phys.* 39(11):7140-7152.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
International Search Report mailed on Mar. 7, 2018, for PCT Application No. PCT/US2017/061848, filed on Nov. 15, 2017, 4 pages.
International Search Report mailed on Jan. 30, 2020, for PCT Application No. PCT/US2019/061180, filed on Nov. 13, 2019, 2 pages.
Non-Final Office Action mailed on Jan. 7, 2020, for U.S. Appl. No. 15/814,222, filed Nov. 15, 2017, 13 pages.
Non-Final Office Action mailed on Dec. 14, 2022, for U.S. Appl. No. 16/887,852, filed May 29, 2020, 12 pages.
Notice of Allowance mailed on Apr. 30, 2020, for U.S. Appl. No. 15/814,222, filed Nov. 15, 2017, 10 pages.
Written Opinion of the International Searching Authority mailed on Mar. 7, 2018, for PCT Application No. PCT/US2017/061848, filed on Nov. 15, 2017, 5 pages.
Written Opinion of the International Searching Authority mailed on Jan. 30, 2020, for PCT Application No. PCT/US2019/061180, filed on Nov. 13, 2019, 5 pages.
Corrected Notice of Allowability mailed on Jan. 30, 2024, for U.S. Appl. No. 16/887,852, filed May 29, 2020, 2 pages.
Notice of Allowance mailed on Dec. 28, 2023, for U.S. Appl. No. 16/887,852, filed May 29, 2020, 9 pages.

THERMAL COOLING RING FOR RADIATION THERAPY SYSTEM

CROSS-REFERENCE TO RELATED APPLICATIONS

This application is a continuation of International Patent Application No. PCT/US2019/061180, filed Nov. 13, 2019, which claims priority to U.S. Provisional Patent Application No. 62/769,269, filed Nov. 19, 2018, the disclosure of each of which is hereby incorporated by reference in its entirety.

BACKGROUND

Radiation therapy involves directing radiation to a tumor from one or more directions. In some radiation therapy systems, a radiation source mounted on a gantry rotates around a patient on a table or couch, and directs radiation toward the patient's tumor(s). As the radiation source rotates around the patient, the patient table or couch may be moved in a direction that is parallel to the axis of rotation of the radiation source. In this manner, radiation may be applied to the patient's tumor(s) from various gantry angles and at various patient table or couch positions, based on images of the patient and the tumor(s) generated by various imaging modalities in advance of the treatment session.

Emission-guided radiation therapy (EGRT) applies radiation based on positron emission paths emitted by a positron emission tomography (PET) tracer that is injected into a patient before a treatment session and preferentially accumulated at one or more tumor(s). In addition to a radiation source that therapeutically irradiates a tumor region, an EGRT system also has one or more arrays of PET detectors to sense emission paths (also known as lines of response or LORs) formed by two coincident, 511 keV photons that originate from positron annihilation events within the tumor region. This emission path data may provide real-time tumor location data. Delivering radiation in response to detected emission paths instead of a complete PET image (which is made of millions of emission paths) may reduce the latency between identifying the location of a tumor and the irradiation of that tumor with the therapeutic radiation source. To timely respond to the detection of an emission path or LOR that indicates the real-time location of a tumor, a gantry of an EGRT system may rotate at speeds ranging from about 10 rotations per minute (RPM) to about 70 RPM. Gantries and components mounted to a gantry may generate significant amounts of heat. Many of the sensors in an EGRT system, however, are sensitive to changes in temperature, and elevated temperatures may negatively impact patient comfort. Thus, there is a desire for a temperature management system that may maintain a temperature of a radiation therapy system (e.g., a gantry, a gantry enclosure, and a treatment bunker within which the gantry and gantry enclosure are disposed) within a comfortable, operable, and safe range.

BRIEF SUMMARY

Disclosed herein are temperature management systems for radiation therapy systems. In some embodiments, an apparatus comprises a stationary frame and a thermal ring. The thermal ring may be rotatably coupled to the stationary frame and disposed relative to the stationary frame such that the thermal ring and the stationary frame define an enclosure. The thermal ring may include a thermally-conductive substrate configured to be in thermal contact with a heat-generating component. Heat from the heat-generating component may be transferred to the stationary frame via the enclosure.

The thermal ring may further comprise a fluid conduit having a sidewall that defines a lumen, wherein at least a portion of the sidewall is in thermal contact with the thermally-conductive substrate. The fluid conduit may be at least partially embedded in the thermally-conductive substrate. The fluid conduit may be located within the thermally-conductive substrate. The thermal ring may have a circumference and the fluid conduit may extend along at least a portion of the circumference. The fluid conduit may be at least partially ring-shaped. The fluid conduit sidewall may include a metal. The stationary frame may be ring-shaped. The fluid conduit may be a first fluid conduit, and the apparatus may further comprise a heat-generating component attached to the thermal ring and a second fluid conduit that thermally connects the heat-generating component with the first fluid conduit. The first fluid conduit and the second fluid conduit may be in fluid communication such that heat generated by the heat-generating component may be transferred to the first fluid conduit via a fluid within the first and second fluid conduits.

A fluid pump may be coupled to at least one of the first fluid conduit or the second fluid conduit, the fluid pump configured to circulate fluid between the first fluid conduit and the second fluid conduit. The stationary frame may include a stationary ring. The stationary ring and the thermal ring may be coaxially disposed. The heat-generating component may be a radiation source. The stationary frame may include a heat exchanger in thermal communication with the enclosure, the heat exchanger configured to deliver air to the enclosure. A rotatable drum may be configured to rotate relative to the stationary frame and the thermal ring may be attached to the rotatable drum.

A plurality of thermally-conductive extending members may be coupled to the thermally-conductive substrate and extend into the enclosure. Each extending member of the plurality of extending members may be cylindrically-shaped. Each extending member of the plurality of extending members may be shaped as a rectangular prism. The plurality of extending members may include at least one hundred extending members.

BRIEF DESCRIPTION OF THE DRAWINGS

FIG. 1A is a perspective view of a variation of a gantry and patient platform.

FIG. 1B depicts a cross-sectional view of the gantry and patient platform of FIG. 1A. FIG. 1C depicts another perspective view of the gantry and patient platform of FIG. 1A.

FIGS. 3A and 3B are a front view and a cross-sectional view, respectively, of a temperature management system. FIG. 3C is a close-up view of the cross-sectional portion identified as 3C in FIG. 3B. FIG. 3D is a the close-up view shown in FIG. 3C with an arrow depicting air flow into an enclosure of the temperature management system.

FIGS. 5A and 5B are a front view and a cross-sectional view, respectively, of a temperature management system. FIG. 5C is a close-up view of the cross-sectional portion identified as 5C in FIG. 5B.

FIGS. 6A and 6B are a front view and a cross-sectional view, respectively, of a temperature management system. FIG. 6C is a close-up view of the cross-sectional portion identified as 6C in FIG. 6B.

DETAILED DESCRIPTION

Figure 1A:
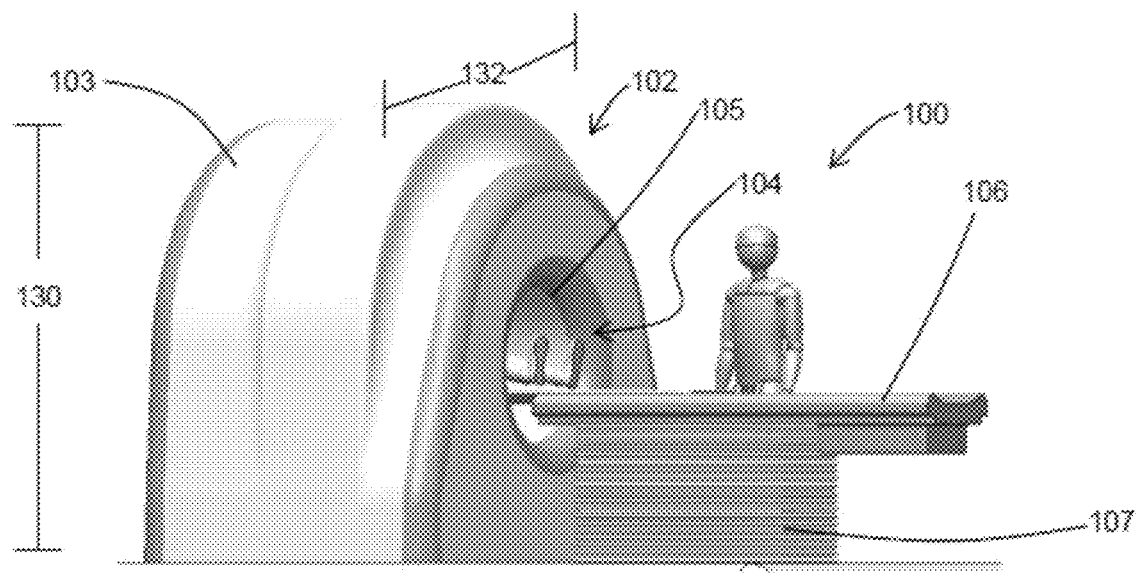
FIGS. 1A-1C are illustrative depictions of variations of an emission-guided radiation therapy system.

Disclosed herein are temperature management systems for radiation therapy systems. In some embodiments, an apparatus comprises a stationary frame and a thermal ring. The thermal ring may be rotatably coupled to the stationary frame and disposed relative to the stationary frame such that the thermal ring and the stationary frame define an enclosure. The thermal ring may include a thermally-conductive substrate configured to be in thermal contact with a heat-generating component. Heat from the heat-generating component may be transferred to the stationary frame via the enclosure.

For example, in some embodiments, a system may include a thermal ring coupled to a rotatable drum on which a heat-generating component is mounted. The rotatable drum and the heat-generating component may be, for example, a rotatable drum and a heat-generating component of a radiation therapy system. The thermal ring may be coupled to the rotatable drum such that the thermal ring rotates with the rotatable drum relative to a stationary frame. Heat generated by the heat-generating component may be transferred to the thermal ring, through the thermal ring, and into an enclosure defined by the thermal ring and the stationary frame. The enclosure may be a bounded space that limits the flow of heated air into an area surrounding the thermal ring and the stationary frame (e.g., the rest of a housing volume enclosing the system and/or a bunker within which the system is disposed). The enclosure may enclose air such that the air is heated by the thermal energy traveling from the thermal ring into the enclosure. The thermal energy may then travel from the air in the enclosure to the stationary frame and/or the heated air may be exchanged for cooler air via, for example, a heat exchanger fluidically coupled to the enclosure. In some embodiments, the enclosure may not be fluidically isolated from an area outside of the thermal ring and the stationary frame (e.g., a gap may exist between the thermal ring and the stationary frame through which air may flow). In some embodiments, a number of extending members (e.g., one hundred extending members) may extend from the thermal ring into the enclosure and may be rotatable with the thermal ring within the enclosure.

Heat may be transferred from the heat-generating component to the thermal ring via fluid traveling through one or more fluid conduits. The fluid conduits may be arranged on the rotatable drum such that fluid within the fluid conduits can draw thermal energy from the heat-generating component and/or the rotatable drum. For example, the fluid conduits may wrap around a base of the heat-generating component, travel through the heat-generating components, and/or may be located sufficiently near the heat-generating component such that fluid (e.g., water) traveling through the fluid conduits can draw heat from the heat-generating component, through a sidewall of the fluid conduit, and into the fluid. The fluid traveling through the fluid conduits near the heat-generating component may have a lower temperature than the heat-generating component such that thermal energy transfers from the heat-generating component to the fluid. Each fluid conduit may also have portions arranged near or in contact with the thermal ring, such that thermal energy can transfer from the fluid, through the sidewall of the fluid conduit, and into the thermal ring. The thermal ring may be formed of a thermally-conductive substrate such that thermal energy can flow from a fluid within the portion of the fluid conduit near or adjacent the thermal ring and through the thermal ring from a higher temperature portion (e.g., near the fluid conduit) to a lower temperature portion (e.g., near the enclosure).

The fluid conduits may each form a fluid loop such that fluid can circulate (e.g., due to being pumped by a fluid pump and/or due to gravity and/or due to centripetal forces as the rotatable drum rotates) between the portion near or adjacent the heat-generating component and the portion near or adjacent the thermal ring. In some embodiments, the portion of each fluid conduit near or adjacent the thermal ring can be arranged on a surface of the thermal ring. In some embodiments, the portion of each fluid conduit near or adjacent the thermal ring can be partially embedded in the thermal ring. In some embodiments, the portion of each fluid conduit near or adjacent the thermal ring can be embedded in the thermal ring such that at least a portion of the fluid conduit is fully surrounded by a substrate forming the thermal ring.

In some embodiments, each of the fluid conduits may include a first fluid conduit (also referred to as a "thermal ring fluid conduit") and a second fluid conduit (also referred to as a "drum-mounted fluid conduit). The first fluid conduit may include the portion near or adjacent the heat-generating component and the second fluid conduit can include the portion near or adjacent the thermal ring. For example, the first fluid conduit may be formed of a flexible material such as, e.g., rubber, and the second fluid conduit can be formed of a thermally-conductive substrate such as, e.g., copper or a copper alloy.

In some embodiments, the heat exchanger may maintain the air in the enclosure at a lower temperature than the temperature of the thermal ring. The air in the enclosure may be maintained at a sufficiently low temperature relative to the thermal ring such that the thermal ring is maintained at a lower temperature than the sidewall of the portion of the fluid conduit within the thermal ring and the sidewall of the portion of the fluid conduit within the thermal ring is maintained at a lower temperature than the temperature of the fluid within the portion of the fluid conduit within the thermal ring (having first been heated by the heat-generating component while in a portion of the fluid conduit near or adjacent to the heat-generating component). Thus, the heat exchanger may maintain a temperature gradient from the heat-generating component, through the fluid in the fluid conduit, through the thermal ring, and to the air in the enclosure such that thermal energy transfers from the heat-generating component to the air in the enclosure. Therefore, the enclosure defined by the thermal ring and the stationary frame may improve the efficiency and/or rate of heat transfer from components on the rotatable drum to the fluid in the fluid conduit as compared to a system in which a thermal ring and stationary frame do not define such an enclosure.

Thus, in use, heat generated by the heat-generating component on the rotatable drum may be transferred to the fluid circulating through the fluid conduit via the sidewall of the portion of the fluid conduit near or adjacent the heat-generating component such that the temperature of the fluid increases. The warmed fluid may then flow from the portion of the fluid conduit near or adjacent the heat-generating component to the portion of the fluid conduit near or adjacent the thermal ring (e.g., under pressure from the fluid pump and/or gravitational forces). As the warmed fluid is circulated from the portion of the fluid conduit near or adjacent the heat-generating component to the portion of the fluid conduit near or adjacent the thermal ring, cooler fluid previously disposed within the portion of the fluid conduit near or adjacent the thermal ring may simultaneously flow into the portion of the fluid conduit near or adjacent the heat-generating component. As the fluid is circulated through the portion of the fluid conduit near or adjacent the thermal ring, thermal energy may transfer from the fluid within the portion of the fluid conduit near or adjacent the thermal ring, through the sidewall of the portion of the fluid conduit near or adjacent the thermal ring, and into the thermal ring such that the temperature of the fluid within the portion of the fluid conduit near or adjacent the thermal ring is reduced. The heat transferred to the thermal ring may then be transferred from the thermal ring to the air that is disposed within the enclosure. The arrangement of the fluid conduit, the thermal ring, the enclosure, the stationary frame, and one or more heat exchangers facilitates heat transfer between the rotatable drum and the stationary frame while limiting heat transfer from the enclosure and/or from the remainder of the system to an area surrounding the thermal ring and the stationary frame (e.g., to an area within a housing enclosing the thermal ring and stationary frame and/or to an area within a bunker within which the arrangement is disposed). Furthermore, the arrangement may facilitate heat transfer across a rapidly-rotating rotatable drum (e.g., a drum rotating at about 60 RPM or more) to the enclosure defined by the thermal ring and the stationary frame.

The air disposed within the enclosure may be circulated within the enclosure (e.g., via the heat exchanger). In embodiments including extending members extending from the thermal ring into the enclosure, at least a portion of the heat transferred to the thermal ring may be first transferred to the extending members, and then transferred from the surfaces of the extending members to the air disposed within the enclosure. For example, as the thermal ring is rotated (e.g., due to being mounted to a rotatable drum), the extending members may also be rotated within the enclosure. The rotation of the extending members within the enclosure may increase heat transfer from the extending members to the air in the enclosure. The extending members may have a surface area and/or a surface-to-volume ratio that favors the transfer of heat from the surface of the extending members into the air within the enclosure such that the heat transfer rate and/or amount from the extending members to the air within the enclosure (and, thus, from the heat-generating component to the fluid within the fluid conduit) is improved. In some embodiments, heated air within the enclosure may be channeled to facility cooling fluid via the heat exchanger. In some embodiments, heat may travel from the air in the enclosure into the stationary frame. The heat may then travel from the stationary frame into the environment surrounding the stationary frame opposite the enclosure (e.g., the room containing the radiation therapy system).

In some embodiments, the arrangement of the fluid conduit, thermal ring, stationary frame, and one or more heat exchangers may draw sufficient heat from the rotatable drum and/or components coupled to the rotatable drum (e.g., heat-generating components) into the enclosure such that the temperature of the rotatable drum, the temperature of components coupled to the rotatable drum, and/or the temperature of an area enclosed by a housing containing the rotatable drum may be reduced (e.g., relative to a system without such a thermal ring arrangement). Furthermore, the noise generated by a system or a portion of a system including or coupled to the arrangement may be reduced relative to a system without such an arrangement. For example, the a system or a portion of a system including or coupled to the arrangement may be reduced from about 3 dBa to about 10 dBa relative to a system without such an arrangement. Additionally, the costs of building and maintaining such a system or a portion of a system including or coupled to the arrangement may be reduced. Moreover, a system or a portion of a system including or coupled to the arrangement may have improved reliability compared to a system lacking such an arrangement. For example, a system or a portion of a system including or coupled to the arrangement may have improved reliability compared to a system including a number (e.g., four) of water-to-air heat exchangers including, e.g., moving motors, bearings, fans, and/or water connections. Because the thermal ring arrangement described herein may have fewer mechanical components than other thermal management systems, the reliability and/or longevity of the system may be prolonged because there are fewer mechanical failure points, fewer components to maintain, and/or fewer components to calibrate.

In some embodiments, the arrangement may draw sufficient heat from the rotatable drum and/or components coupled to the rotatable drum (e.g., heat-generating components) into the enclosure such that the temperature of the rotatable drum, the temperature of components coupled to the rotatable drum, and/or the temperature of an area enclosed by a housing containing the rotatable drum may be maintained below a threshold temperature. For example, the temperature of the heat-generating components may be maintained between about 35 degrees Celsius and 40 degrees Celsius. Other components, such as PET detectors, may be maintained at a temperature between about 24 degrees Celsius and about 26 degrees Celsius. In some embodiments, the temperature of the components coupled to the rotatable drum may be maintained below a threshold temperature and/or within a target temperature range by a combination of the arrangement and one or more additional cooling subsystems or devices, such as Peltier cooling units coupled to the components coupled to the rotatable drum. Furthermore, the arrangement may reduce discomfort to the patient by preventing the temperature of the air near the patient (e.g., the air in an interior opening of the rotatable drum within which a patient may be disposed) from rising above a threshold temperature. For example, the temperature within a bore or channel of the rotatable drum (e.g., within which a patient may be disposed) may be maintained within 5 degrees Celsius of the ambient temperature of the treatment room within which the rotatable drum is disposed.

Generally, the systems and methods described herein may be configured for use with a radiation therapy system, such as any of the radiation therapy systems shown and/or described in U.S. patent application Ser. No. 15/814,222, filed Nov. 15, 2017, which is hereby incorporated by reference in its entirety. For example, the systems and methods described herein may be configured for use with a radiation therapy system comprising a gantry having a stationary frame and rotatable ring coupled to the stationary frame via a rotating mechanism, a therapeutic radiation source (e.g., a megavolt (MV) X-ray source) mounted on the rotatable ring, and one or more PET detectors mounted on the rotatable ring. The radiation therapy system may also comprise a MV detector mounted on the rotatable ring opposite the therapeutic radiation source. The beam emitted from the therapeutic radiation source may be shaped by one or more jaws, and/or a multi-leaf collimator (e.g., a binary multi-leaf collimator), and/or any number of beam-shaping components, such as additional collimators or jaws, as may be desirable. The rotating mechanism may comprise a slip ring and a drive train that are capable of rotating the ring from about 10 RPM to about 70 RPM. The rotatable ring may rotate about a patient treatment area, which may comprise a bore or channel through the gantry. The gantry may be enclosed within a housing that may have a housing bore or channel that corresponds to the gantry bore or channel. The gantry housing may be a mechanical and/or visual barrier between the patient and the gantry.

A radiation therapy system may also comprise a patient platform that is configured to move the patient into and out of the patient treatment area. The position of the patient platform within the bore or channel of the gantry, the position of the radiation source (which may be a therapeutic radiation source) around the patient treatment area (e.g., circumferential location of the radiation source around the gantry bore or channel) and the radiation pulses from the radiation source may be timed by a controller such that a desired dose is delivered to a desired region of the patient (e.g., a tumor region). In some variations, the rotatable ring may be configured to continuously rotate 360 degrees in one or more directions (e.g., clockwise and/or counterclockwise), while in other variations, the rotatable ring may be configured to rotate less than 360 degrees in one or more directions (e.g., rotate clockwise about 270 degrees and counterclockwise about 270 degrees, rotate clockwise about 150 degrees from a vertical axis and counterclockwise about 135 degrees from the vertical axis, rotate clockwise about 180 degrees from the vertical axis and about 150 degrees from the vertical axis, etc.).

The one or more PET detectors may be mounted along at least a portion of the circumference of the rotatable ring (e.g., inner circumference, outer circumference, or any location between the inner and outer circumference). The location of the PET detectors with respect to the length of the bore or patient area may be the same as the location of the MV or therapeutic radiation source and MV detector (e.g., on the same "slice" of the rotating ring). That is, the radiation beam emitted by the therapeutic radiation source may be on the same plane as the PET detectors. The PET detectors may be arranged to avoid intersecting with the radiation beam path, and instead, a MV detector may be located in the therapeutic radiation beam path. In some variations, the PET detectors may span a subset of the circumference of the ring (e.g., 180 degrees). For example, a first array of PET detectors may be mounted on a first segment or length of the rotatable ring that has a length of about 25% of the circumference of the ring and a second array of PET detectors may be mounted on a second segment or length of the ring that has a length of about 25% of the circumference of the ring. In this variation, the portion of the ring circumference that is covered by PET detectors is about 50% of the circumference. The first and second arrays of PET detectors may be located generally opposite each other (e.g., directly opposite each other, such that the center of each of the PET detector arrays are about 180 degrees from each other), or alternatively, the first array of PET detectors may be offset from the second array of PET detectors so that they are not opposite each other (e.g., the center of each of the PET detector arrays are less than about 180 degrees from each other, for example, about 45 degrees, about 90 degrees, or about 120 degrees, or about 150 degrees, etc.). In variations where the PET detectors are not on the same plane or "slice" of the rotating ring as the therapeutic radiation source (i.e., where the PET detectors are not co-planar with the therapeutic radiation source), the PET detectors may span the entire circumference of the ring (e.g., 360 degrees).

Figure 1B:
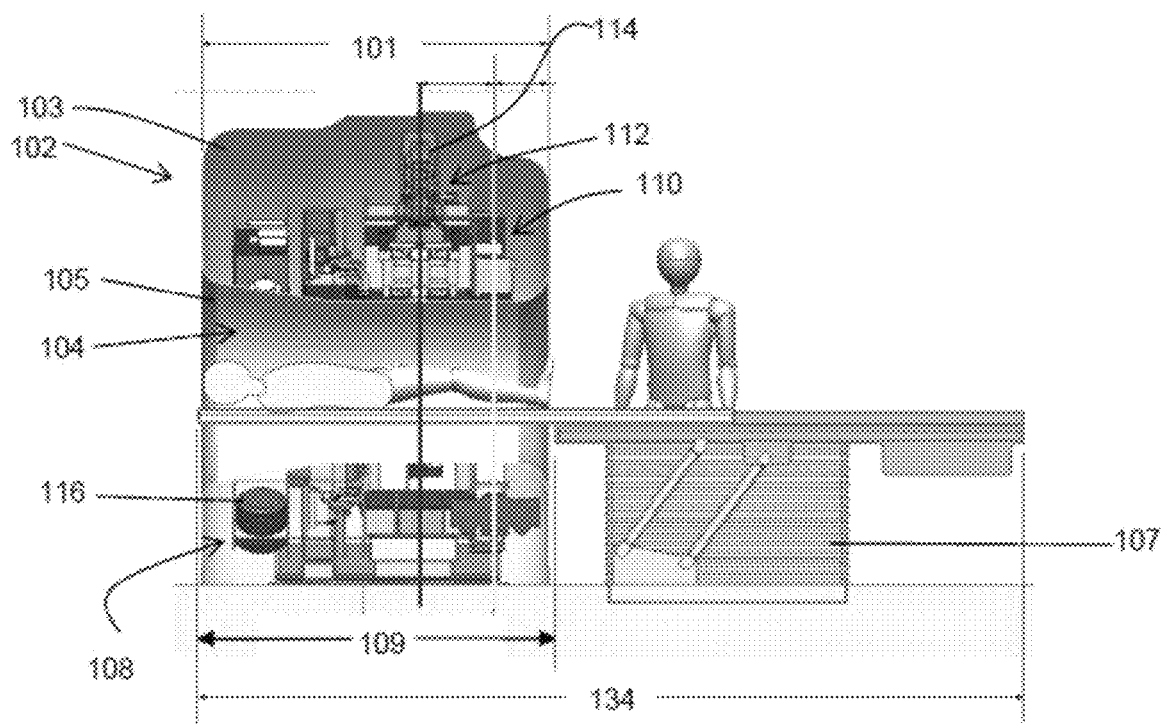

FIGS. 1A-B depict one variation of a radiation therapy system 100 (which may be an emission-guided radiation therapy system) which may be used with the systems and methods described herein. The radiation therapy system 100 comprises a gantry 102 enclosed within a housing 103, a patient treatment area 104 within a bore 105 of the gantry, and a patient platform 106. The gantry 102 may be a rotatable gantry, such as a circular gantry, comprising a stationary frame 108 and a rotatable ring 110 that may be configured to continuously rotate 360 degrees clockwise or counterclockwise (e.g., continuously rotating) from about 10 RPM to about 70 RPM with respect to the stationary frame 108. The housing 103 may have a shape that generally follows the contours of the gantry 102 such the patient platform 106 may be advanced into and out of the bore 105. Enclosed within the internal volume of the housing 103 and depicted in FIG. 1B, the radiation therapy system 100 may further comprise a therapeutic X-ray source or radiation source 112 such as a linear accelerator (linac) 114 mounted on the rotatable ring 110 at a first longitudinal location along the bore 105 and an imaging X-ray source or radiation source 116 mounted on the rotating ring 110 at a second longitudinal location along the bore 105. In this variation, the radiation beams generated by the imaging radiation source 116 may not be co-planar with the radiation beams generated by the therapeutic radiation source 112. The length 101 of the bore 105 may be between about 120 cm and about 210 cm. In some variations, the length 101 of the bore 105 may be about 185 cm. In some variations, the length 101 of the bore 105 may be less than or equal to about 226 cm. In some variations, the length 101 of the bore 105 may be equal to about 225 cm. A diameter of the bore 105 may be between about 60 cm and about 120 cm. In some variations, a diameter of the bore 105 may be about 85 cm. The patient platform 106 may be configured to extend from the platform base 107 such that the extension length 109 may be between about 150 cm and 250 cm. In some variations, the extension length 109 may be about 190 cm. In some variations, the extension length 109 may be about 199 cm. The housing 103 may have a height 130 of between about 220 cm and about 280 cm. In some variations, the housing 103 may have a height of about 250 cm. In some embodiments, the housing 103 may have a height of about 257 cm. The housing 103 may have a width 132 of between about 225 cm and 325 cm. In some variations, the housing 103 may have a width 132 of about 276 cm. In some variations, the housing 103 may have a width 132 of about 298 cm. The housing 103 may have a length between about 120 cm and 230 cm. In some variations, the housing 103 may have a length of about 185 cm. In some variations, the housing 103 may have a length of about 225 cm. The length 134 of the radiation therapy system 100, including the gantry and the patient platform may be between about 400 cm and about 500 cm. In some variations, the length 134 of the radiation therapy system 100 may be about 439 cm. In some variations, the length 134 of the radiation therapy system 100 may be about 494 cm. In some variations, the depth of a portion of the treatment room (e.g., a pit, such as a concrete-walled hole, formed in the treatment room and extending downward from the floor of the treatment room and providing clearance for rotating components mounted to the gantry 102) may be such that the axis of the bore 105 is about 110 cm from the bottom of the system 100. In some variations, the axis of the bore 105 may be about 88.2 cm from the bottom of the system 100. In some variations, the depth of the portion (e.g., the pit) of treatment room relative to the floor of the treatment room may be between about 10 cm and 60 cm. In some variations, the depth may be about 32 cm. In some variations, the depth of the portion (e.g., the pit) of treatment room relative to the floor of the treatment room may be about 38 cm.

Figure 1C:
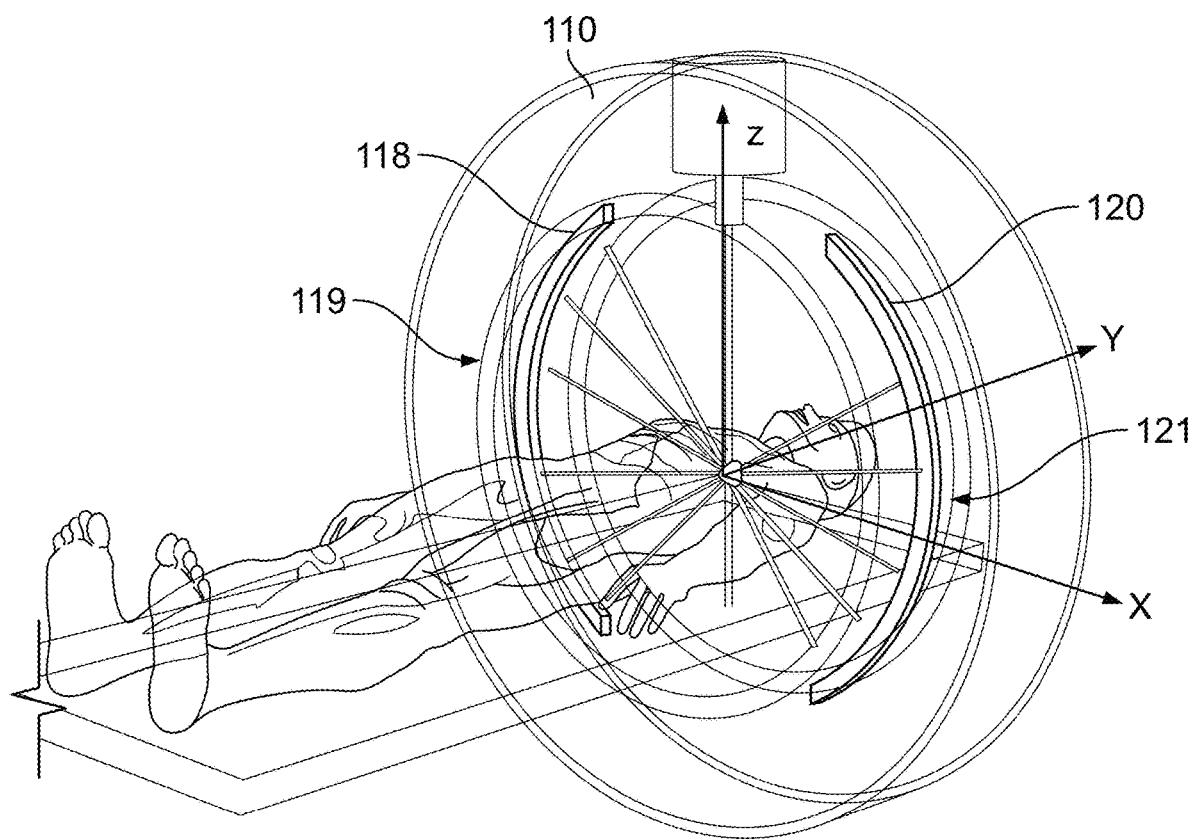

The radiation therapy system 100 may also comprise one or more PET detectors mounted on the rotating ring 110. For example, as depicted in FIG. 1C, the system 100 may comprise a first array 118 of PET detectors mounted along a first length 119 of the circumference (e.g., inner circumference) of the rotating ring and a second array 120 of PET detectors mounted along a second length 121 of the circumference (e.g., inner circumference) of the rotating ring. The first array 118 may be located directly across from (e.g., 180 degrees from) the second array. The length of the first and second arrays may be the same or may be different. In the variation in FIG. 1C, the length of the first and second arrays is the same, and each may have a length that is about 25% of the inner circumference of the rotating ring 110. The arc occupied by the first array 118 (and the second array 120) may have an angular sweep of about 90 degrees, but may have any desired angular sweep (e.g., from about 45 degrees to about 180 degrees, about 60 degrees, about 75 degrees, about 120 degrees, about 135 degrees, about 140 degrees, about 150 degrees, about 155 degrees, etc.). In other variations, the PET detectors 118, 120 may be arranged around the entire length of circumference of the ring except for the portions of the circumference that may be occupied by the therapeutic radiation source and a MV detector located opposite the therapeutic radiation source. In some variations, one or more PET detector arrays or modules mounted on the rotatable ring may be co-planar with the radiation beam emitted by the therapeutic radiation source, and may each provide approximately 25% coverage (e.g., 50% coverage together) azimuthally such that as they rotate, they are compatible with being co-planar with the radiotherapy beamline (i.e., the PET detector arrays or modules are not located in the therapeutic beam path). That is, each array may cover about 25% of the total angular sweep of the rotatable gantry. The width of the PET detector arrays or modules (i.e., along the length of the bore) may be selected at least in part to help facilitate the acquisition and detection of PET events (e.g., emission paths). For example, the width of the PET detector arrays or modules may be between about 4 cm and about 20 cm. In some variations, the width of the PET detector arrays or modules may be about 5 cm. In one variation, a radiation therapy system may comprise two PET detector arrays, each PET detector array comprising a plurality of PET detector modules, and each PET detector module may comprise a subarray of PET detectors. For example, each PET detector array may comprise 32 PET detector modules (for a total of 64 PET detector modules) and in each PET detector module may comprise a 6×12 subarray of PET detectors.

Alternatively, PET detector arrays may be located on a separate ring or gantry from the therapeutic radiation source and/or MV detector. In some variations, the PET detector ring or gantry may be non-rotatable while in other variations, the PET detector ring or gantry or may rotatable. A rotatable PET detector ring or gantry may rotate in concert or synchrony with the therapeutic radiation source ring or gantry. For example, the PET ring or gantry may be mechanically mounted to the therapeutic radiation source ring or gantry such that rotating one of the gantries causes rotation of the other. Alternatively, the PET ring or gantry may be separately rotatable from the therapeutic radiation source ring or gantry. For example, a motion controller may rotate the two gantries or rings together or separately, as may be desirable.

Optionally, in addition to a therapeutic radiation source, a radiation therapy system may comprise a kV X-ray source or imaging radiation source mounted on the rotatable ring and a kV X-ray detector also located on the rotatable ring opposite to the kV X-ray source or imaging radiation source. The radiation from the kV X-ray source or imaging radiation source may be emitted along a first plane, while the radiation from the therapeutic radiation source may be emitted along a second plane. The first plane and the second plane may not be co-planar. For example, the imaging radiation source may be mounted on a rotatable ring at a first longitudinal location of the bore or channel extending through the gantry, while the therapeutic radiation source may be mounted a rotatable ring at a second longitudinal location of the bore or channel. The rotatable ring(s) to which the imaging radiation source and the therapeutic radiation source are mounted may be the same or different rotatable rings, which may be configured to rotate together (e.g., in synchrony) or rotate independently (e.g., rotation of one gantry is separate from rotation of the other gantry). The first and second planes may be generally parallel to each other, or may be at a non-zero angle with respect to each other. In other variations, the first plane and the second plane may be co-planar. For example, the imaging radiation source may be mounted at the same longitudinal location of the bore or channel as the therapeutic radiation source. Alternatively or additionally, there may be a single X-ray source or radiation source that may be used to treat patient regions with radiation, as well as help to provide data that may be used for image or dose reconstruction. The radiation therapy system may comprise a kV detector mounted on the rotatable ring opposite the kV or imaging radiation source. Data from the kV detector may be used for registering the position of the patient within the radiation therapy system, and/or generating an anatomical image of the patient. Although the MV radiation source may be described as a therapeutic radiation source, it should be understood that data acquired as a result of irradiation from the MV radiation source may be used in the computation and generation of images and/or dose maps. The therapeutic radiation source may be any type of ionizing radiation, for example, photon radiation (e.g., X-rays and gamma rays) and/or particle radiation (e.g., electrons, protons, neutrons, carbon ions, alpha particles, and beta particles).

A radiation therapy system may comprise a controller in communication with the gantry. The controller may comprise one or more processors and one or more machine-readable memories in communication with the one or more processors. The controller may be connected to the gantry by wired or wireless communication channels. The controller may be located in the same room or bunker as the gantry, or may be located in a different room or bunker from the gantry. In some variations, the controller may be located on the gantry, and may be, for example, mounted on the stationary frame of the gantry. The controller may be configured to coordinate the movement of the couch with the rotation of the gantry (e.g., speed), activate the radiation source(s), open or close collimator leaves/jaws, detect the position of the collimator leaves/jaws, detect positron emission paths, detect MV radiation applied to the patient, compute delivered dose based on detected MV radiation data, store treatment plan data, anatomical data from other imaging modalities including, but not limited to, MRI, CT, ultrasound, etc. The transfer of data and command signals between the stationary frame and the rotating ring may be facilitated by one or more communication interfaces that are configured to continuously transmit signals while the ring is rotating. Real-time positron emission data collected by the PET detectors and/or gantry rotational data (e.g., speed) and/or gantry positional data (e.g., gantry angle) may be transmitted across the one or more communication interfaces to the controller. The controller may use such data to update radiation delivery, for example, by adjusting the rotation speed of the ring, opening or closing certain leaves of a multi-leaf collimator disposed over the therapeutic radiation source, and/or by adjusting the timing of the therapeutic radiation pulses.

Generally, the radiation therapy systems described herein may comprise a gantry comprising attachment or mounting assemblies that may help to reduce the effect of vibrational and/or centripetal forces of a rapidly rotating ring (e.g., about 50 RPM, about 60 RPM, about 70 RPM) that may cause shifts in position. For example, the components mounted on a ring rotating at about 60 RPM or more may be subject to greater levels of centripetal forces than on a gantry rotating at slower speeds (e.g., about 10 RPM, about 20 RPM). The components mounted on the rotatable ring, such as the radiation source(s), various detector(s) (e.g., MV detectors, kV detectors, PET detectors), as well as the multi-leaf collimator(s), jaw(s), linac, and all supporting structures, may have a total weight on the order of about two tons. Rotating two tons on a ring having a diameter of about 1.4 meters at a speed of about 60 RPM may generate forces that may cause deflections on the ring itself, and may also generate forces that could impact the reliable functioning of the ring-mounted components. The various component and sub-systems of the radiation therapy system described herein may comprise specialized mount assemblies and/or arrangements and/or orientations to help mitigate the effect of these forces. In some variations, the gantry may also comprise motors or actuators to facilitate positional adjustments of radiation source(s) should they shift or become misaligned with other components of the radiation therapy system (e.g., multi-leaf collimator(s), jaw(s), detector(s)). While some radiation therapy systems may comprise all of the components described herein, it should be understood that some variations may comprise a subset of these components, as may be desired.

Some radiation therapy systems may comprise a continuously-rotating gantry comprising a rotatable ring and a stationary frame (e.g., the radiation therapy system 100 described above). The gantry may be configured to rotate 360 degrees or more in one or more directions (e.g., capable of rotating 360 degrees or more counterclockwise and/or rotating 360 degrees or more clockwise). A continuously-rotating gantry may receive its rotational force from a traditional motor and coupled drive system or from an integrated rotor and stator design. For example, a continuously-rotating gantry may comprise one or more embedded magnetic elements or inductive elements located on the rotatable ring. The stationary frame of the gantry may comprise embedded inductive elements or magnetic elements. In this arrangement, the rotatable ring may rotate with respect to the stationary frame in a similar fashion as a rotor rotates with respect to a stator of a rotary system. To reduce latencies from the time a lesion or target region is located to therapeutic radiation delivery, the system may rotate the therapeutic radiation source and delivery hardware at much higher speeds than traditional radiotherapy systems. A radiation therapy system may comprise rotor and stator elements that are integrated into the same structure that supports the bearings, which may help the gantry rotate several tons of hardware continuously (e.g., 360 degrees) at speeds up to about 70 RPM (e.g., at least about 50 RPM, about 60 RPM, etc.).

Rotating the therapeutic radiation source and delivery hardware at higher speeds may generate greater levels of heat than traditional radiotherapy systems; a continuously-rotating gantry for radiotherapy may present a challenging temperature or thermal management problem. A gantry that is capable of rotating at speeds from about 10 RPM to about 70 RPM may generate greater amounts of heat than a gantry rotating at slower speeds. For example, a continuously-rotating radiation therapy system may produce over 70 KW of heat. Many of the sensors in the radiation therapy system are sensitive to changes in temperature, and elevated temperatures may negatively impact patient comfort as well. Temperature management systems that have been used in radiation therapy systems with low-speed gantries (e.g., less than about 10 RPM), may not be suitable for use with high-speed gantries (e.g., about 20 RPM to about 70 RPM, about 60 RPM or more). For example, large-bore, continuously-rotating fluid unions, which have been used in radiation therapy systems with low-speed gantries, may not be effective at managing the temperature of a radiation therapy system including a high-speed gantry. Furthermore, the continuously-rotating fluid unions used in radiation therapy systems with low-speed gantries may not be configured to reliably and/or effectively operate when used in radiation therapy systems with gantries rotating at a higher rotational speed (e.g., at 60 RPM). For example, continuously-rotating fluid unions may be configured to have a maximum operational speed (e.g., in RPMs) and thus may not be rated for operation at higher speeds above the maximum operational speed. Furthermore, continuously-rotating fluid unions may be expected to fail after a certain number of rotations, and/or a range of a number of rotations, and a gantry rotating at a higher rotational speed may reach the expected failure number of rotations and/or the expected failure range of number of rotations much sooner than a gantry rotating at a lower rotational speed. Thus, continuously-rotating fluid unions intended for use with a gantry rotating at a lower rotational speed may have too short of a life span (e.g., too small of an expected failure number of rotations and/or too small of an expected failure range of number of rotations) to be effective in conjunction with a gantry rotating at a higher rotational speed. Additionally, some known systems utilize water-to-air heat exchangers disposed on a rotating gantry to convert thermal energy of fluid disposed within fluid conduits coupled to the rotating gantry to hot air. The hot air is contained within sealed system covers, and additional water-to-air heat exchangers may then transfer the thermal energy of the hot air within the sealed system cover to city water. Furthermore, some known tomotherapy systems use water-to-air heat exchangers to "dump" hot air into a treatment room containing the tomotherapy system. These systems, however, require a clinic facility including the treatment room to increase the thermal capacity of the treatment room, which may be expensive and/or unavailable in some facilities. Additionally, these known systems have high material costs, are often unreliable, and may generate high levels of audible noise. Thus, there is a need for a temperature management system with lower material costs, greater reliability, higher performance, and reduced audible system noise.

Figure 2A:
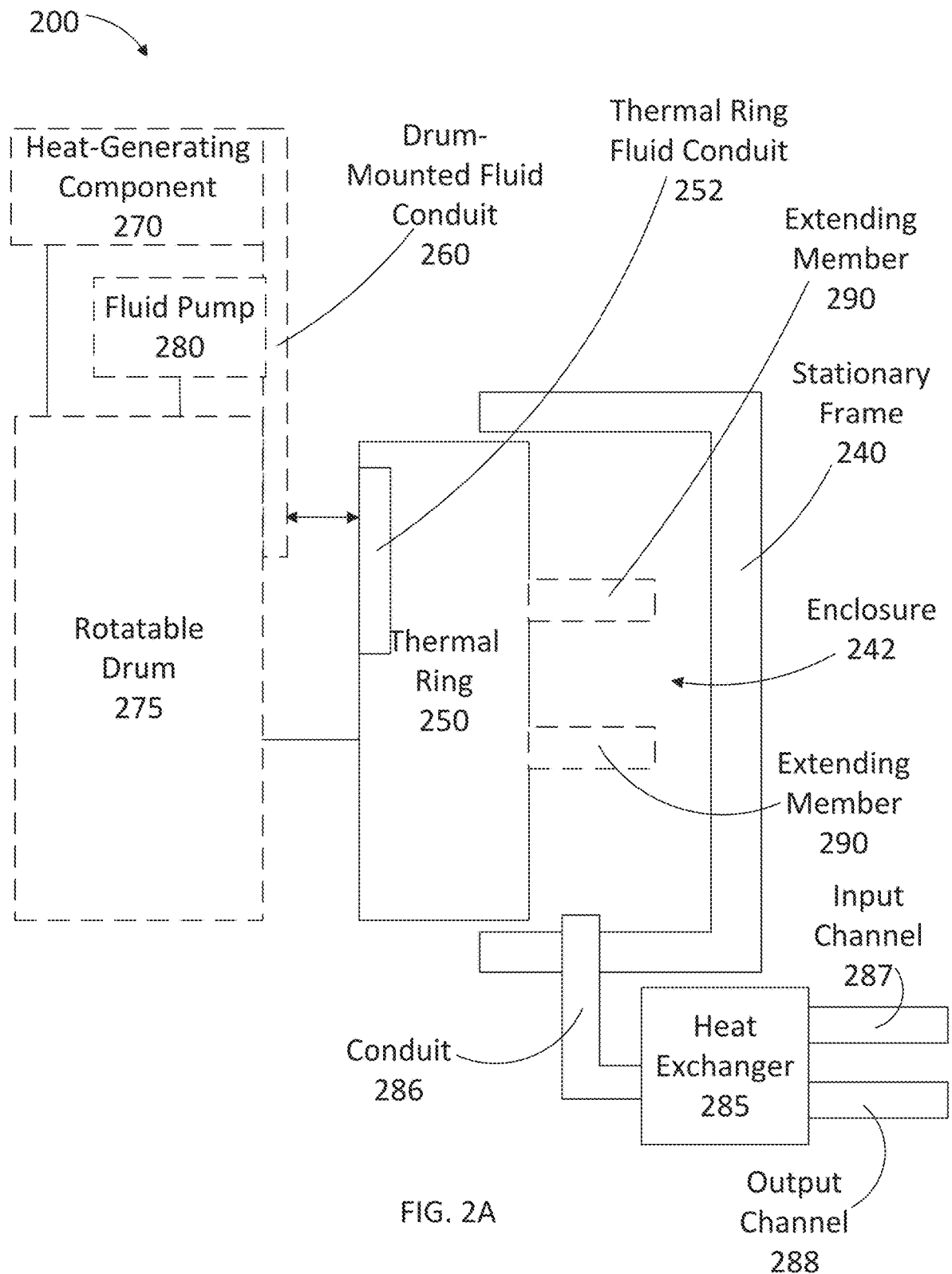
FIG. 2A is a schematic representation of a temperature management system, according to an embodiment.

FIG. 2A is a schematic representation of a temperature management system 200. The temperature management system 200 may be used with any of the radiation therapy systems described herein, such as, for example, the radiation therapy system shown and described with respect to FIGS. 1A-1C. The system 200 includes a stationary frame 240 and a thermal ring 250. The thermal ring 250 may be coupled to the stationary frame 240 and disposed relative to the stationary frame 240 such that the thermal ring 250 and the stationary frame 240 define an enclosure 242. The thermal ring 250 may include a thermally-conductive substrate configured to be in thermal contact with a heat-generating component, such as heat-generating component 270. In some embodiments, the thermally-conductive substrate of the thermal ring 250 may be, for example, a copper alloy. Heat from the heat-generating component 270 may be transferred to the stationary frame 240 via the enclosure 242.

In some embodiments, the stationary frame 240 may include a sidewall, an inner wall, and an outer wall. The inner wall and the outer wall may project from the sidewall toward the thermal ring 250 such that the inner wall, the outer wall, the sidewall, and the thermal ring 250 collectively define the enclosure 242. In some embodiments, the enclosure 242 may be a bounded space that limits the flow of heated air (e.g., air heated via heat transfer from the thermal ring 250) into an area surrounding the thermal ring 250 and the stationary frame 240 (e.g., the rest of a housing volume enclosing the system 200 and/or bunker within which the system 200 is disposed). In some embodiments, the enclosure 242 is not entirely enclosed such that some heater air can flow from the enclosure to the area surrounding the thermal ring 250 and the stationary frame 240 (e.g., via a gap between the thermal ring 250 and the stationary frame 240). In some embodiments, the enclosure 242 may be an entirely enclosed space such that the enclosure 242 is fluidically isolated from an area surrounding the thermal ring 250 and the stationary frame 240 except for, optionally, a heat exchanger configured to exchange the heater air for cooler air. In some embodiments, the stationary frame 240 and the thermal ring 250 may each be ring-shaped such that the stationary frame 240 and the thermal ring 250 each define an opening or a bore. For example, an inner surface of the inner wall of the stationary frame 240 may define an opening (i.e., a bore) in the stationary frame 240. An inner surface of the thermal ring 250 may define an opening (i.e., a bore) in the thermal ring 250. When assembled such that the thermal ring 250 and the stationary frame 240 collectively define the enclosure 242, the opening in the stationary frame 240 and the opening in the thermal ring 250 may be coaxially arranged and configured to receive a patient within each of the openings.

The thermal ring 250 may be arranged relative to the stationary frame 240 such that a gap is defined between the thermal ring 250 and the stationary frame 240. Thus, in some variations, air may flow between the enclosure 242 and an area external to the system 200 (e.g., a bunker within which the system 200 is disposed) via the gap. In some variations, the thermal ring 250 may have an inner diameter sufficiently large and an outer diameter sufficiently small such that the thermal ring 250 may be disposed at least partially between an outer surface of the inner wall of the stationary frame 240 and an inner surface of the outer wall of the stationary frame 240.

The thermal ring 250 may be coupled to a rotatable drum 275 of a radiation therapy system, such as any of the radiation therapy systems described herein. The rotatable drum 275 may be, for example, a rotatable gantry, such as any of the rotatable gantries described herein. The rotatable drum 275 may be configured to rotate relative to the stationary frame 240 (e.g., via a traditional motor and coupled drive system and/or an integrated rotor and stator design). The thermal ring 250 may be coupled to the rotatable drum 275 via any suitable method such that rotation of the rotatable drum 275 causes corresponding rotation of the thermal ring 250. For example, in some embodiments the thermal ring 250 may be mounted to the rotatable drum 275 via welding and/or one or more mechanical fasteners (e.g., screws). In some embodiments, the system 200 may include a thermal insulation between the thermal ring 250 and the rotatable drum 275. The thermal insulation may include, for example, a solid substrate having low thermal conductivity. For example, the thermal insulation may include rigid polyimide, fiberglass, and/or polyethylene. In some embodiments, the thermal conductivity of the thermal insulation may range from between about 0.05 W/(m·K) and about 0.5 W/(m·K). The thermal ring 250 may be mounted to the rotatable drum 275 such that a bore of the rotatable drum 275 is aligned with the opening of the thermal ring 250 and the stationary frame 240 (e.g., such that the bore of the rotatable drum 275 and the opening of the thermal ring 250 are coaxial). The heat-generating component 270 may be disposed on the rotatable drum 275 such that the heat-generating component 270 and the thermal ring 250 are coupled via at least the rotatable drum 275. In some embodiments, the rotatable drum 275 may include a thermally-conductive substrate such that heat may be transferred from the heat-generating component 270 to the rotatable drum 275. Heat may also be transferred from the rotatable drum 275 to the thermal ring 250.

The thermal ring 250 may include a thermal ring fluid conduit 252 (also referred to as a "first fluid conduit"). In some variations, the thermal ring fluid conduit 252 may include a sidewall defining a lumen, and the thermal ring fluid conduit 252 may be at least partially disposed within the thermal ring 250. At least a portion of the sidewall of the thermal ring fluid conduit 252 may be in thermal contact with the thermally-conductive substrate of the thermal ring 250. For example, in some embodiments, the thermal ring fluid conduit 252 may be at least partially embedded in the thermally-conductive substrate of the thermal ring 250 such that a portion of an outer surface of the sidewall of the thermal ring fluid conduit 252 is in direct contact with the thermally-conductive substrate of the thermal ring 250. In some embodiments, the thermal ring fluid conduit 252 may be located within the thermally-conductive substrate of the thermal ring 250. For example, an outer surface of the sidewall of the thermal ring fluid conduit 252 may be at least partially surrounded by the thermally-conductive substrate of the thermal ring 250. In some embodiments, the thermal ring 250 has a circumference, and the thermal ring fluid conduit 252 extends along at least a portion of the circumference. In some embodiments, the thermal ring 250 may be at least partially ring-shaped. In some variations, the thermal ring fluid conduit 252 includes an inlet on a first end of the thermal ring fluid conduit 252 and an outlet on a second end of the thermal ring fluid conduit 252. The inlet and the outlet of the thermal ring fluid conduit 252 may be disposed at or near a surface of the thermal ring 250 such that a portion of the lumen of the thermal ring fluid conduit 252 partially or completely embedded within the thermal ring 250 is fluidically accessible via the inlet and outlet. The sidewall of the thermal ring fluid conduit 252 may be formed of a material capable of transferring heat from within the thermal ring fluid conduit 252 to the thermal ring 250. For example, the sidewall of the thermal ring fluid conduit 252 may include a metal, such as, for example, copper, stainless steel, and/or brass.

In some variations, the thermal ring fluid conduit 252 may be defined by the thermal ring 250. For example, the thermal ring fluid conduit 252 may be machined directly into the thermal ring 250. The thermal ring 250 may include fluid couplings (e.g., tubes and/or tube connectors) coupled to each end of the thermal ring fluid conduit 252. The thermal ring fluid conduit 252 may have ends (e.g., openings in a sidewall of the thermal ring 250) sealed by a braised or soldered end cap. The braised or soldered end cap may include and/or be coupleable to fluid couplings (e.g., tubes and/or tube connectors). The braised or soldered end cap may be configured to be coupled to a drum-mounted fluid conduit 260 (described below) such that fluid may flow between the drum-mounted fluid conduit 260 and the thermal ring fluid conduit 252. Such an embodiment may have fewer parts and greater thermal efficiency than embodiments in which a thermal rings 250 includes an embedded thermal ring fluid conduit 252 and/or is coupled to a thermal ring fluid conduit 252.

In some embodiments, the thermal ring 250 may include a number of thermal ring portions such that the thermal ring 250 may be serviced more easily. For example, the thermal ring 250 may include a first half and a second half, each of the halves having an outer perimeter shaped as a half circle. Each of the halves may be separately mounted to the rotatable drum 275 and may include and/or be coupled to portions of the thermal ring fluid conduit 252 (described below). The portions of the thermal ring fluid conduits 252 within each of the halves may be coupled to each other via fluid couplings.

The system 200 may include a drum-mounted fluid conduit 260 (also referred to as a "second fluid conduit"). The drum-mounted fluid conduit 260 includes a sidewall that defines a lumen. The drum-mounted fluid conduit 260 has a first end and a second end, and may be fluidically coupled to the thermal ring fluid conduit 252 via the first end and the second end of the drum-mounted fluid conduit 260. For example, the first end and the second end of the drum-mounted fluid conduit 260 may be coupled to the inlet and the outlet of the thermal ring fluid conduit 252, respectively, such that the thermal ring fluid conduit 252 and the drum-mounted fluid conduit 260 may form at least a portion of a fluid loop and fluid may flow between the thermal ring fluid conduit 252 and the drum-mounted fluid conduit 260. The drum-mounted fluid conduit 260 may be arranged such that at least a portion an exterior surface of the drum-mounted fluid conduit 260 is in contact with the rotatable drum 275 and/or the heat-generating component 270 such that the drum-mounted fluid conduit 260 thermally connects the rotatable drum 275 and/or the heat-generating component 270 with the thermal ring fluid conduit 252. Thus, heat generated by the heat-generating component 270 may be transferred to the thermal ring fluid conduit 252 via the sidewall of the thermal ring fluid conduit 252 and a fluid transferrable between the thermal ring fluid conduit 252 and the drum-mounted fluid conduit 260.

In some embodiments, the heat-generating component 270 may be, for example, a radiation source. In some embodiments, the heat-generating component 270 may be, for example, a radiation source such as a linear accelerator (linac), a kV system, a converter target, and/or a PET system. In some embodiments, the system 200 may include any suitable number of heat-generating components 270.

In some embodiments, the system 200 may include a plurality of thermally-conductive extending members 290 coupled to the thermally-conductive substrate of the thermal ring 250 and extending into the enclosure 242. Although FIG. 2 shows the system 200 includes two extending members 290, the system 200 may include any suitable number of extending members 290. For example, the system 200 may include one hundred extending members 290. In some embodiments, the system 200 may include over one hundred extending members 290. In some embodiments, the extending member 290 may be formed as pins. The extending members 290 may have any suitable shape or combination of shapes. For example, in some embodiments, the extending members 290 may be cylindrically-shaped. In some embodiments, the extending members 290 may be shaped as rectangular prisms. In some embodiments, the extending members 290 may have a textured surface or define any suitable number of pores or through-holes to facilitate heat transfer from the extending members 290 to the air in the enclosure 242.

The extending members 290 may be shaped such as to increase the surface-to-volume ratio of each extending member 290 so that there is greater surface area in contact with the volume of the enclosure 242 (e.g., air) to facilitate heat transfer from the extending members 290 into the enclosure 242. For example, the extending members 290 may include undulating curved surfaces and/or a zigzag surfaces (e.g., forming a triangle wave or sawtooth wave). In some embodiments, the projecting portions may extend laterally from the extending members 290. For example, tuft-like structures, branched structures, and/or tetrahedron (i.e., pyramid-shaped) projections may extend from the extending members 290. In some embodiments, rod-shaped projections may extend from each extending member 290 perpendicularly and/or at a non-perpendicular angle relative to the central axis of the extending member 290.

In some embodiments, the stationary frame 240 may include a heat exchanger 285. The heat exchanger 285 may be configured to reduce the temperature of the thermal ring 250 and/or the extending members 290 (such that the temperature of the heat-generating component 270 and/or the rotatable drum 275 may be correspondingly reduced) via forced convection. The heat exchanger 285 may be in thermal communication with the enclosure 242. For example, the heat exchanger 285 may be configured to deliver air to the enclosure 242 via a conduit 286. The heat exchanger 285 may be an air-to-water heat exchanger. For example, the heat exchanger 285 may include an inflow duct, one or more coils, and a fan. The one or more coils may be filled with a chilled fluid (e.g., water) and may be formed of a thermally-conductive substrate (e.g., copper). As shown in FIG. 2A, the heat exchanger 285 may be fluidically coupled to an input channel 287 and an output channel 288 such that chilled fluid may be provided to the one or more coils via the input channel 287 and fluid may flow from the one or more coils via the output channel 288. The input channel 287 may be a facility water input channel and the output channel 288 may be a facility water output channel. The fan, which may be, for example, an axial-flow fan or a centrifugal fan, may force air across the coils such that the air is cooled as thermal energy is transferred from the air to the coils and into the chilled fluid. Having been reduced in temperature, the air may continue to travel through the conduit 286 and into the enclosure 242. The heat exchanger 285 can also include an exhaust duct so that, as the cool air is forced into the enclosure 242, warmer air within the enclosure 242 can be pushed out of the enclosure via the exhaust duct. In some embodiments, the heat transfer rate from the thermal ring 250 and/or the extending members 290 may depend, at least in part, on the flow rate of air, the air-to-water heat exchange rate, and/or the temperature of air provided by the heat exchanger 285 to the enclosure 242. The heat exchanger 285 may be configured to deliver air to the enclosure 242 at any suitable flow rate and/or temperature. For example, the heat exchanger 285 may provide air at a temperature below the temperature of the thermal ring 250 and/or the extending members 290 such that thermal energy may transfer from the thermal ring 250 and/or the extending member 290 into the air in the enclosure 242. In some embodiments, the heat exchanger 285 may include one or more coils filled with a chilled fluid and a fan, the chilled fluid can be maintained at a temperature sufficiently low and/or the air can be forced over the one or more coils at a sufficiently high flow rate such that the air delivered over the coils and to the enclosure 242 has a temperature below that of the thermal ring 250 and/or the extending members 290.

In some embodiments, the system 200 may include a fluid pump 280 fluidically coupled to the drum-mounted fluid conduit 260. The fluid pump 280 may be configured to circulate fluid through a loop formed by the thermal ring fluid conduit 252 and the drum-mounted fluid conduit 260 such that heat may be transferred from the heat-generating component 270 to the sidewall of the thermal ring fluid conduit 252 via circulating fluid between the drum-mounted fluid conduit 260 and the thermal ring fluid conduit 252. The fluid may be, for example, water. In some variations, the fluid may be heated to, for example, about 40° C. by the heat-generating component 270 and/or the rotatable drum 275 prior to being circulated from the drum-mounted fluid conduit 260 to the thermal ring fluid conduit 252. In some embodiments, the fluid pump 280 may be mounted to the thermal ring 250. In some embodiments, the fluid pump 280 may be mounted to the rotatable drum 275. In some embodiments, the fluid pump 280 may include any suitable type of fluid pump. In some embodiments, the fluid pump 280 may include a three phase, 480V centrifugal pump. The fluid pump 280 may have a minimum flow rate of, for example, 50 liters/minute. In some embodiments, the fluid pump 280 may include an AC or DC piston pump, a cavity pump, and/or a gear pump.

Although only one fluid loop is described (including the thermal ring fluid conduit 252 and the drum-mounted fluid conduit 260), the system 200 may include any suitable number of fluid loops. For example, the thermal ring 250 may include any suitable number of fluid conduits similar to the thermal ring fluid conduit 252. The fluid conduits of the thermal ring 250 may each be coupled to a fluid conduit arranged in contact with a heat-generating component such as the heat-generating component 270 and/or the rotatable drum 275 similarly to the drum-mounted fluid conduit 260. Increasing the number of fluid loops (each including a thermal ring fluid conduit 252 and a drum-mounted fluid conduit 260) in the system 200 may facilitate heat transfer such that the rate of heat transfer from the heat-generating component 270 (and any additional heat-generating components mounted on the rotatable drum 275) to the thermal ring 250 may increase.

In some embodiments, the system 200 may include temperature and/or air flow sensors where sensor data may be used to adjust the operation of the heat exchanger 285 (e.g., air-to-water heat exchange rate and/or air flow rate) and/or the fluid pump 280 (e.g., rate of fluid flow through the thermal ring fluid conduit 252 and/or the drum-mounted fluid conduit). For example, temperature and/or air flow sensors may be disposed within the enclosure 242 (e.g., on a surface of the thermal ring 250 and/or on a surface of the stationary frame 240 defining the enclosure 242), on or near each heat-generating component 270, in various locations on the rotatable drum 275, within an enclosure defining a space within which the system 200 is disposed, or in any other suitable location.

Figure 2B:
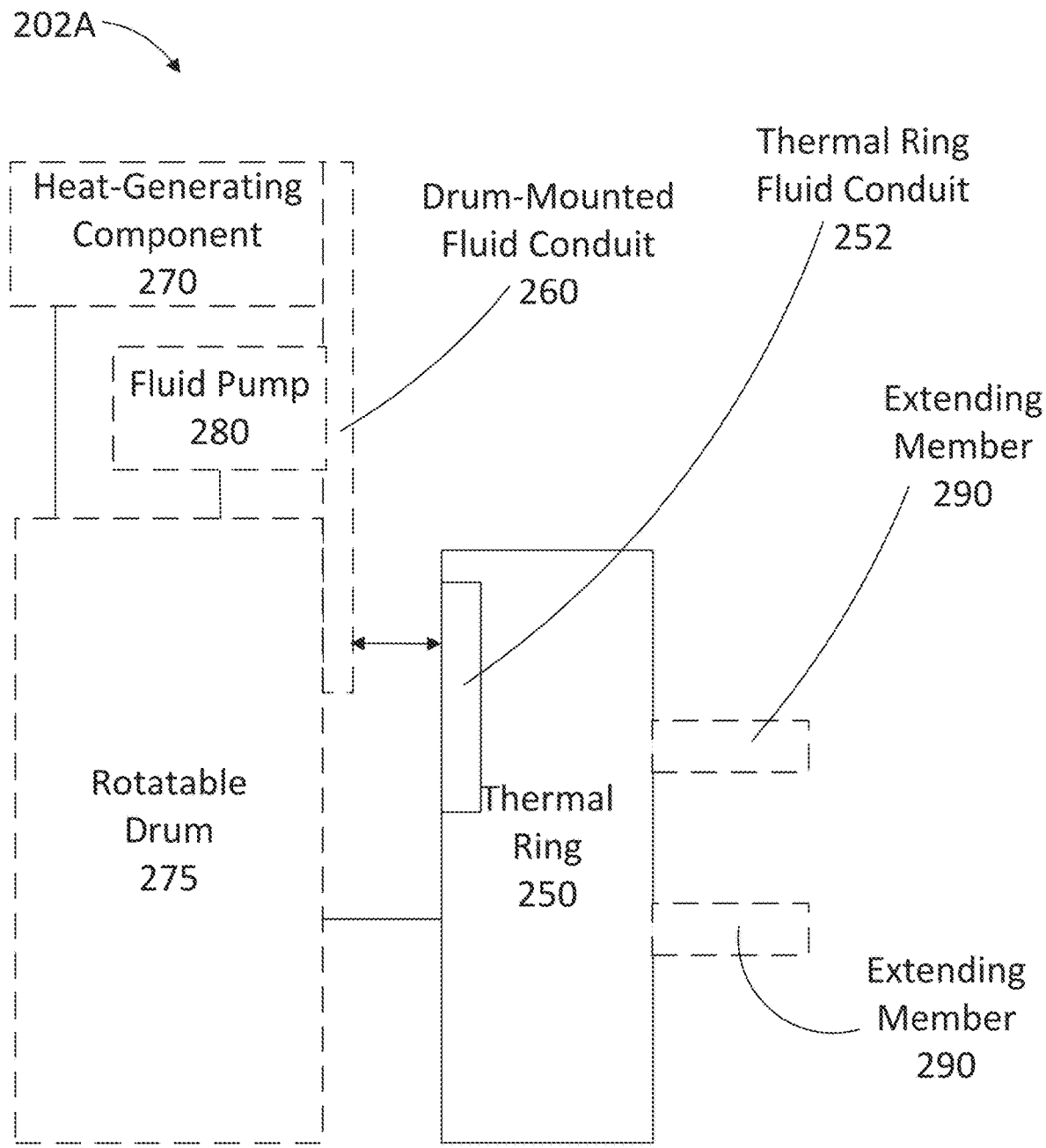
FIG. 2B is a schematic representation of a rotatable subsystem of the system of FIG. 2A.
Figure 2C:
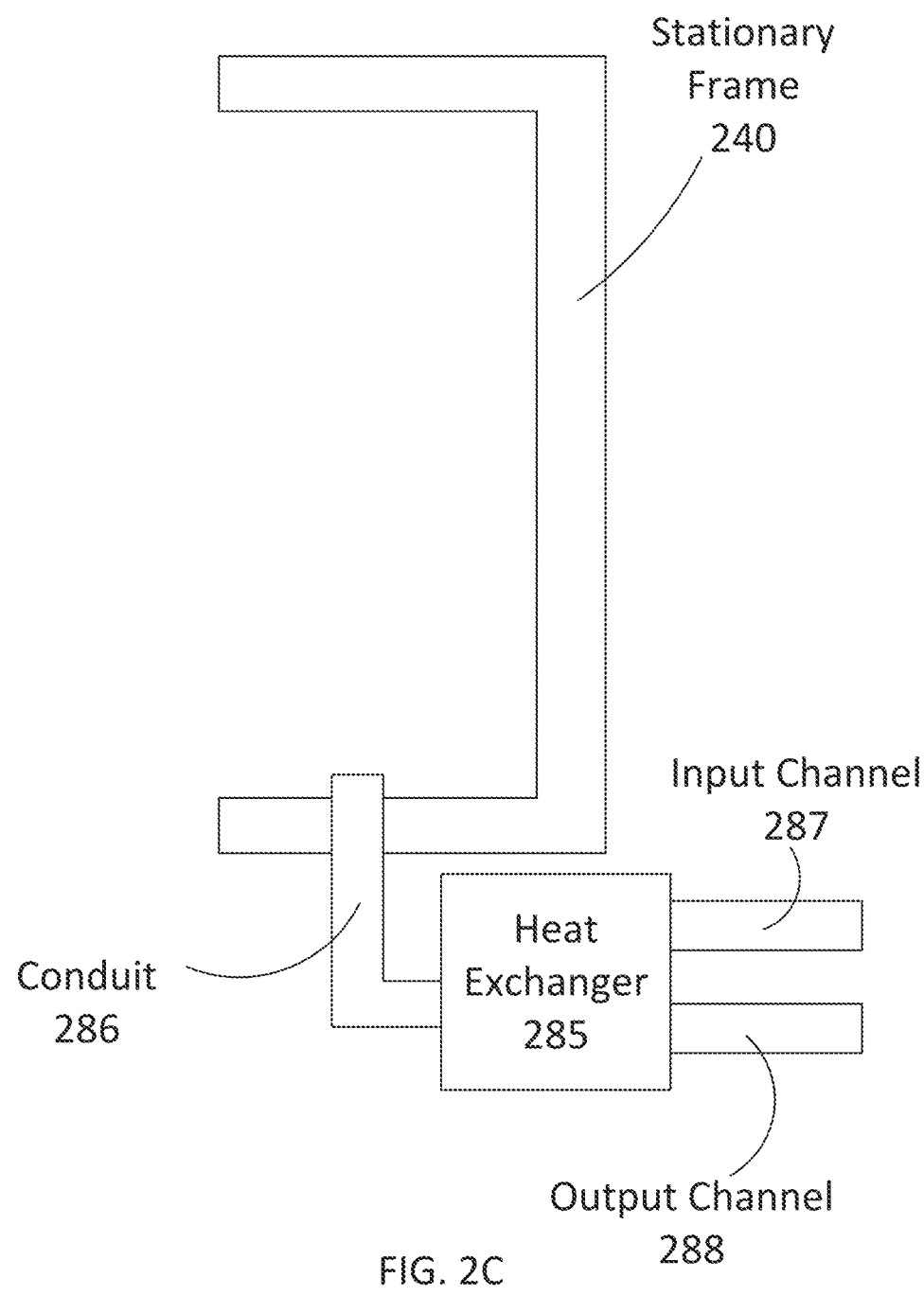
FIG. 2C is a schematic representation of a stationary subsystem of the system of FIG. 2A.

FIGS. 2B and 2C are schematic representations of a rotatable subsystem 202A and a stationary subsystem 202B, respectively, of the system 200. The rotatable subsystem 202A may include, for example, the thermal ring 250 and the thermal ring fluid conduit 252. The rotatable subsystem 202A may also include the extending members 290, the rotatable drum 275, the fluid pump 280, the heat-generating component 270, and/or the drum-mounted fluid conduit 260. The stationary subsystem 202B may include, for example, the stationary frame 240. The stationary subsystem 202B may also include the heat exchanger 285. During operation of the system 200, the rotatable subsystem 202A is configured to rotate relative to the stationary subsystem 202B.

In use, heat generated by a heat-generating component 270 on the rotatable drum 275 may be transferred to a fluid circulated through the drum-mounted fluid conduit 260 via a sidewall of the drum-mounted fluid conduit 260 such that the temperature of the fluid increases. Without wishing to be bound by theory, during this stage, the fluid within the drum-mounted fluid conduit 260 may generate a temperature gradient such that heat is transferred from the heat-generating component 270 to the fluid. The warmed fluid may then flow from the drum-mounted fluid conduit 260 to the thermal ring fluid conduit 252 (e.g., under pressure from the fluid pump 280). As the warmed fluid is circulated from the drum-mounted fluid conduit 260 to the thermal ring fluid conduit 252, cooler fluid previously disposed within the thermal ring fluid conduit 252 may simultaneously flow into the drum-mounted fluid conduit 260. The warmed fluid may be a higher temperature than the thermal ring 250 such that, as the fluid is circulated through the thermal ring fluid conduit 252, thermal energy may transfer from the fluid within the thermal ring fluid conduit 252, through the sidewall of the thermal ring fluid conduit 252, and into the thermal ring 250 such that the temperature of the fluid within the thermal ring fluid conduit 252 is reduced. The thermal ring 250 may be a higher temperature than the air in the enclosure 242, such that the heat transferred to the thermal ring 250 may then be transferred to air that is disposed within the enclosure 242 and circulated (e.g., via the heat exchanger 285) between the thermal ring 250 and the stationary frame 240. In embodiments including extending members 290, the heat transferred to the thermal ring 250 may be first transferred to the extending members 290, and then transferred from the extending members 290 to the air disposed within the enclosure 242. In some embodiments, heated air within the enclosure 242 may be channeled to facility cooling fluid via the heat exchanger 285.

In some embodiments, the heat exchanger 285 may maintain the air in the enclosure 242 at a sufficiently low temperature relative to the thermal ring 250 such that the thermal ring 250 is maintained at a lower temperature than the sidewall of the thermal ring fluid conduit 252 and the sidewall of the thermal ring fluid conduit 252 is maintained at a lower temperature than the temperature of the fluid within the thermal ring fluid conduit 252 (having first been heated by the heat-generating component 270 while in the drum-mounted fluid conduit 260). Thus, the heat exchanger 285 may maintain a temperature gradient from the heat-generating component 270, through the drum-mounted fluid conduit 260, through the fluid circulating through the drum-mounted fluid conduit 260 and the thermal ring fluid conduit 260, through the thermal ring fluid conduit 260, through the thermal ring 250, and to the air in the enclosure 242 such that thermal energy transfers from the heat-generating component 270 to the air in the enclosure 242.

Figure 3A:
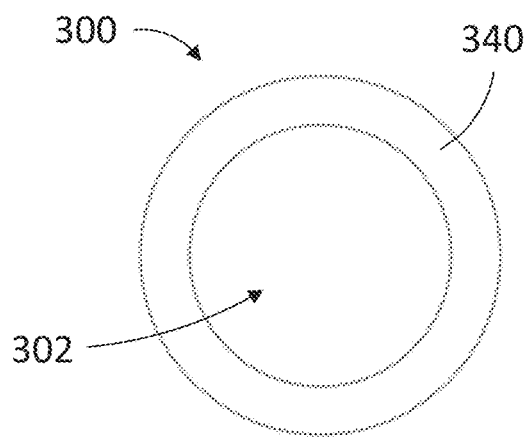
FIGS. 3A-3D are illustrative depictions of a temperature management system, according to an embodiment.
Figure 3B:
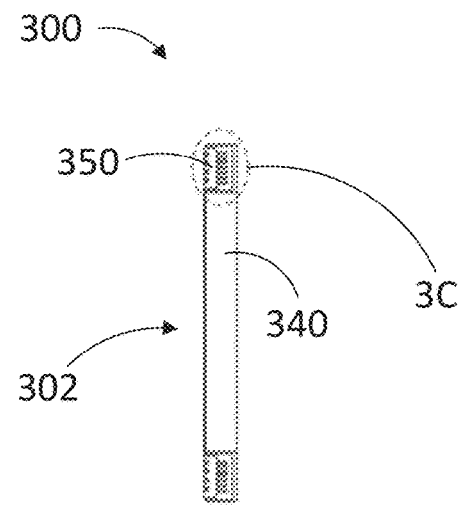

FIGS. 3A and 3B are a front view and a cross-sectional view, respectively, of a temperature management system 300. The temperature management system 300 may be used with any of the radiation therapy systems described herein, such as, for example, the radiation therapy system shown and described with respect to FIGS. 1A-1C. The system 300 may be the same or similar in structure and/or function to any of the temperature management systems described herein, such as, for example, the system 200. The system 300 includes a stationary frame 340 and a thermal ring 350. The thermal ring 350 is coupled to the stationary frame 340, and the stationary frame 340 and the thermal ring 350 are each ring-shaped such that the system 300 defines an opening 302. In some embodiments, the stationary frame 340 may have a maximum outer diameter of, for example, about 71", and a minimum inner diameter of, for example, about 55". In some embodiments, the maximum thickness of the stationary frame 340 and the thermal ring 350, when assembled as shown in FIG. 3B, may be about 4.5". In some embodiments, the combination of the stationary frame 340 and the thermal ring 350, when assembled as shown in FIG. 3B, may occupy a space having a volume of about 7,000 to about 9,000 cubic inches. For example, the combination of the stationary frame 340 and the thermal ring 350, when assembled as shown in FIG. 3B, may occupy a space having a volume of about 8,000 cubic inches. The distance between the sidewall 341 and the wall of the thermal ring 350 facing the sidewall 341 may range from about 1" to about 2". The extending members 390 may have a length ranging from about ¾" to about 1¾". The nominal clearance between the free end of each extending member 390 and the sidewall 341 may be about ¼".

Figure 3C:
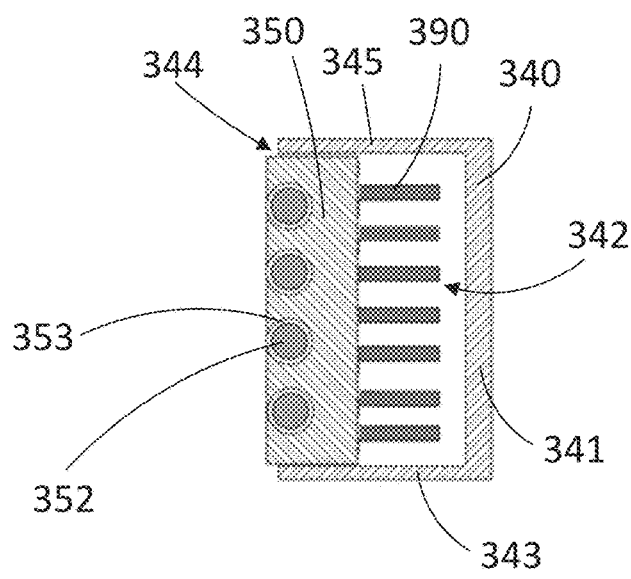

As shown in FIG. 3C, which is a close-up view of the cross-sectional portion identified as 3C in FIG. 3B, the thermal ring 350 is disposed relative to the stationary frame 340 such that the thermal ring 350 and the stationary frame 340 define an enclosure 342. The enclosure 342 may correspond to the shape of the stationary frame 340 (e.g., may be ring-shaped). The stationary frame 340 includes a sidewall 341, an inner wall 343, and an outer wall 345. The inner wall 343 and the outer wall 345 may project from the sidewall 341 such that the inner wall 343, the outer wall 345, the sidewall 341, and the thermal ring 350 collectively define the enclosure 342. In some embodiments, the enclosure 342 defines a space through which air may be forced. As shown in FIG. 3C, the enclosure 342 may be a bounded space that limits and/or prevents the flow of heated air into an area surrounding the thermal ring 350 and the stationary frame 340 (e.g., a housing volume outside of the enclosure 342 enclosing the system 300 and/or a bunker within which the system 300 is disposed). The enclosure 342 may define a space within which air may be exchanged by, e.g., a heat exchanger that is smaller in volume than the volume of the housing, bunker, and/or room within which the system 300 is disposed. The enclosure 342 may be sufficiently large such that enough air can be forced through the enclosure 342 to reduce the temperature of the thermal ring 350 via convection and create a sufficient temperature gradient between a heat-generating component on a rotatable drum to which the thermal ring 350 is coupled and the enclosure 342 (e.g., through fluid conduits 352, sidewalls 353, and the thermal ring 350) to effectively manage the temperature of the heat-generating component.

The thermal ring 350 may be arranged relative to the stationary frame 340 such that a gap 344 is defined between the thermal ring 350 and the stationary frame 340. Thus, air may flow between the enclosure 342 and an area external to the system 300 (e.g., a bunker within which the system 300 is disposed) via the gap 344. As shown in FIGS. 3B and 3C, the thermal ring 350 may have an inner diameter sufficiently large and an outer diameter sufficiently small such that the thermal ring 350 may be disposed at least partially between an outer surface of the inner wall 343 of the stationary frame 340 and an inner surface of the outer wall 345 of the stationary frame 340.

The thermal ring 350 may be coupled to a rotatable drum of a radiation therapy system, such as a rotatable drum of any of the radiation therapy systems described herein. The rotatable drum may be, for example, a rotatable gantry, such as any of the rotatable gantries described herein. The rotatable drum may be configured to rotate relative to the stationary frame 340. The thermal ring 350 may be coupled to the rotatable drum via any suitable method such that rotation of the rotatable drum causes corresponding rotation of the thermal ring 350. For example, the thermal ring 250 may be mounted to the rotatable drum via welding and/or one or more screws. The thermal ring 350 may be mounted to the rotatable drum such that a bore of the rotatable drum is aligned with the opening of the thermal ring 350 and the stationary frame 340 (e.g., such that the bore of the rotatable drum and the opening of the thermal ring 350 are coaxial). A heat-generating component, such as any of the heat-generating components described herein, may be disposed on the rotatable drum such that the heat-generating component and the thermal ring 350 are coupled via the rotatable drum. The thermal ring 350 includes a thermally-conductive substrate configured to be in thermal contact with the heat-generating component such that heat from a heat-generating component may be transferred to the stationary frame 340 from the thermal ring 350 via the air in the enclosure 342. For example, heat may be transferred (away) from the heat-generating component to the stationary frame 340 via a fluid in one or more fluid conduits.

The thermal ring 350 may include a number of thermal ring fluid conduits 352 (also referred to as "first fluid conduits") such that the thermal ring 350 may be in thermal contact with one or more heat-generating components via, at least in part, the thermal ring fluid conduits 352 and a corresponding set of drum-mounted fluid conduits (also referred to as second fluid conduits) coupled to the thermal ring fluid conduits 352 and arranged partially adjacent to the one or more heat-generating components. As shown in FIG. 3C, each of the thermal ring fluid conduits 352 may include a sidewall 353 defining a lumen. Each of the thermal ring fluid conduits 352 may be at least partially disposed within the thermal ring 350. As shown in FIG. 3C, at least a portion of the sidewall 353 of each thermal ring fluid conduit 352 is in thermal contact with the thermally-conductive substrate of the thermal ring 350. Each thermal ring fluid conduit 352 is at least partially embedded in the thermally-conductive substrate of the thermal ring 350 such that a portion of an outer surface of each sidewall 353 of each thermal ring fluid conduit 352 is in direct contact with the thermally-conductive substrate of the thermal ring 350. The outer surface of the sidewall 353 of each thermal ring fluid conduit 352 may be at least partially surrounded by the thermally-conductive substrate of the thermal ring 350. In some embodiments, the thermal ring 350 has a circumference, and each thermal ring fluid conduit 352 extends along at least a portion of the circumference. In some embodiments, the thermal ring 350 may be at least partially ring-shaped. In some variations, each thermal ring fluid conduit 352 includes an inlet on a first end of the thermal ring fluid conduit 352 and an outlet on a second end of the thermal ring fluid conduit 352. The inlet and the outlet of each thermal ring fluid conduit 352 may be disposed at or near a surface of the thermal ring 350 such that a portion of the lumen of each thermal ring fluid conduit 352 partially or completely embedded within the thermal ring 350 is fluidically accessible via the inlet and outlet. The sidewall 353 of each thermal ring fluid conduit 352 may be formed of a material capable of transferring heat from within the thermal ring fluid conduit 352 to the thermal ring 350. For example, the sidewall of each thermal ring fluid conduit 352 may include a metal, such as, for example, copper. Although the system 300 is shown as including four thermal ring fluid conduits 352, the system 300 may include any suitable number of thermal ring fluid conduits 352 (e.g., 2, 4, 6 or more). In some embodiments, rather than each thermal ring fluid conduit 352 being coupled to separate drum-mounted fluid conduits (described below), two or more of the thermal ring fluid conduits 352 can be coupled to one another (e.g., the outlet of one to the inlet of another) by one or more connecting conduits. In some embodiments, rather than including a number of separate thermal ring fluid conduits 352, the system 300 can include one thermal ring fluid conduit 352 disposed in, for example, a spiral arrangement within or adjacent to the thermal ring 350. The one thermal ring fluid conduit 352 can have one inlet and one outlet.

As described above, the system 300 may include or be coupled to a number of drum-mounted fluid conduits (not shown). The drum-mounted fluid conduits may be the same or similar in structure and/or function to any of the drum-mounted fluid conduits described herein (e.g., the drum-mounted fluid conduit 260). For example, each drum-mounted fluid conduit may include a sidewall that defines a lumen. Each drum-mounted fluid conduit may have a first end and a second end, and may be fluidically coupled to one of the thermal ring fluid conduits 352 via the first end and the second end of the drum-mounted fluid conduit. For example, the first end and the second end of each drum-mounted fluid conduit may be coupled to the inlet and the outlet of a thermal ring fluid conduit 352, respectively, such that the thermal ring fluid conduit 352 and the drum-mounted fluid conduit form at least a portion of a loop and fluid may flow between each thermal ring fluid conduit 352 and each respective drum-mounted fluid conduit. Each drum-mounted fluid conduit may be arranged such that at least a portion of each drum-mounted fluid conduit is in contact with a rotatable drum and/or a heat-generating component (such as any of the rotatable drums and/or heat-generating components described herein) such that the drum-mounted fluid conduit thermally connects the rotatable drum and/or the heat-generating component with one of the thermal ring fluid conduits 352. Thus, heat generated by the heat-generating component may be transferred to each thermal ring fluid conduit 352 via a fluid transferrable between each thermal ring fluid conduit 352 and each corresponding drum-mounted fluid conduit.

Figure 3D:
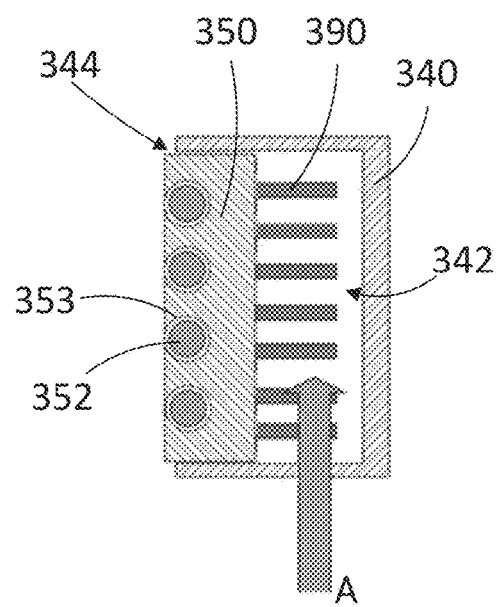

In some embodiments, the stationary frame 340 may include a heat exchanger (not shown). The heat exchanger may be the same or similar in structure and/or function to any of the heat exchangers described herein, such as the heat exchanger 285. The heat exchanger may be in thermal communication with the enclosure 342. For example, as shown in FIG. 3D, the heat exchanger may be configured to deliver air to the enclosure 342 in the direction of arrow A. The heat exchanger may be an air-to-water heat exchanger. The heat exchanger may provide cooled air to the enclosure 342 (e.g., air at a lower temperature than the thermal ring 350 such that thermal energy is transferred from the thermal ring 350 to the air in the enclosure 342). In some embodiments, the stationary frame 340 may include an inlet and an outlet such that cooled air can be provided to the enclosure 342 via the inlet and air (e.g., warmed air) can escape or be drawn from the enclosure 342 via the outlet.

In some embodiments, the system 300 may include a fluid pump fluidically coupled to each drum-mounted fluid conduit. The fluid pump may be the same or similar in structure and/or function to any fluid pumps described herein, such as the fluid pump 280. Each fluid pump may be configured to circulate fluid through a corresponding loop formed by a thermal ring fluid conduit 352 and a drum-mounted fluid conduit such that heat may be transferred from a heat-generating component to a corresponding thermal ring fluid conduit 352 via circulating fluid between each drum-mounted fluid conduit and each thermal ring fluid conduit 352. The fluid may be, for example, water. In some variations, the fluid may be heated to, for example, about 40° C. by the heat-generating component prior to being circulated through each thermal ring fluid conduit 352.

As shown, the system 300 includes a plurality of thermally-conductive extending members 390 coupled to the thermally-conductive substrate of the thermal ring 350 and extending into the enclosure 342. The thermally-conductive extending members 390 can be the same or similar in structure and/or function to the extending members 290 described above with respect to FIG. 2. For example, The system 300 may include any suitable number of extending members 390 (e.g., one hundred or more). and the extending members 390 may have any suitable shape or combination of shapes.

In use, the system 300 may function the same or similarly as described above with respect to the system 200 shown in FIG. 2. For example, the air disposed within the enclosure 342 may be maintained at a sufficiently low temperature relative to the thermal ring 350 such that the thermal ring 350 is maintained at a lower temperature than the sidewall 353 of each thermal ring fluid conduit 352 and the sidewall 353 of each thermal ring fluid conduit 352 is maintained at a lower temperature than the temperature of the fluid within each thermal ring fluid conduit 352. Thus, a temperature gradient may be generated and maintained from the fluid in each thermal ring fluid conduit 352, through each sidewall 353, through the thermal ring 350, through the extending members 390, and to the air in the enclosure 342 such that thermal energy flows from the fluid in each thermal ring fluid conduit 352 to the air in the enclosure 342. Due to this temperature gradient, the fluid in each thermal ring fluid conduit 352 may flow through a respective drum-mounted fluid conduit to a heat-generating component and draw thermal energy form the heat-generating component such that the temperature of the heat-generating component is reduced. The heated fluid may then flow back to each thermal ring fluid conduit 352 and be cooled due to the temperature gradient through each thermal ring fluid conduit 352, through each sidewall 353, through the thermal ring 350, through the extending members 390, and to the air in the enclosure 342.

Figure 4:
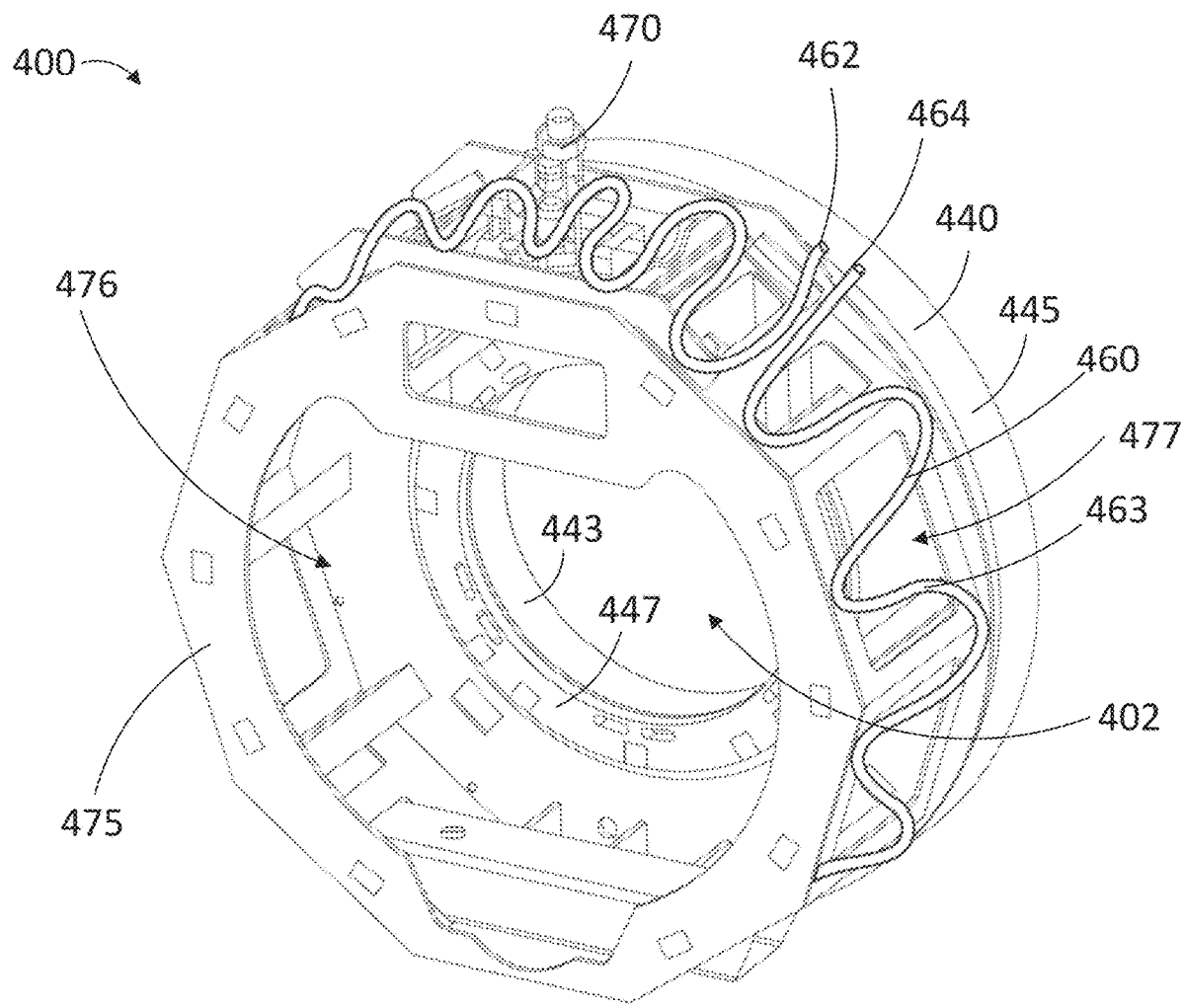
FIG. 4 is a perspective view of a temperature management system, according to an embodiment.

FIG. 4 is a perspective view of a system 400. The system 400 may be the same or similar to any of the systems described herein, such as, for example, the system 200 and/or the system 300. For example, the system 400 includes a stationary frame 440 and a rotatable drum 475 that may be the same or similar in structure and/or function to any of the stationary frames or rotatable drums, respectively, described herein. A heat-generating component 470 (e.g., a linac) may be coupled (e.g., mounted) to the rotatable drum 475 such that the heat-generating component 470 rotates with the rotatable drum 475. As shown in FIG. 4, the rotatable drum 475 may define an opening or bore 476 and the stationary frame 440 may define an opening 402. The bore 476 and the opening 402 may be aligned (e.g., coaxial) such that the a patient may be received within the bore 476 and the opening 402.

The rotatable drum 475 may be coupled to a thermal ring (not shown). The thermal ring may be the same as any of the thermal rings described herein, such as, for example, the thermal ring 350 described above with respect to the system 300. The thermal ring is coaxial with the stationary frame and may be disposed at least partially within an interior formed by the stationary frame 440. As shown in FIG. 4, the stationary frame 440 includes an outer wall 445 and an inner wall 443. The stationary frame 440 may also include a sidewall similar to sidewall 341 discussed above with respect to the system 300 on a back surface of the stationary frame 440. The thermal ring may be coupled (e.g., mounted) to a back surface of a portion 477 of the rotatable drum 475 such that the thermal ring and the stationary frame 440 form an enclosure and the thermal ring may rotate with the rotatable drum 475 relative to the stationary frame 440.

The thermal ring may also include a thermal ring fluid conduit (also referred to as a "first fluid conduit") disposed within or defined by the thermal ring. The thermal ring fluid conduit may be the same or similar in structure and or function to any of the thermal ring fluid conduits described herein, such as, for example, the thermal ring fluid conduits 352 described above with respect to the system 300. The thermal ring fluid conduit may include and/or define an inlet and an outlet such that fluid may flow into the thermal ring fluid conduit via the inlet and fluid may flow out of the thermal ring fluid conduit via the outlet. In some embodiments, the thermal ring may include any suitable number of thermal ring fluid conduits, each having an inlet and an outlet.

As shown in FIG. 4, the system 400 includes a drum-mounted fluid conduit 460 (also referred to as a "second fluid conduit"). The drum-mounted fluid conduit 460 may be the same or similar in structure and/or function to any of the drum-mounted fluid conduits described herein, such as, for example, the drum-mounted fluid conduit 260 described above. For example, the drum-mounted fluid conduit 460 has an inlet 462 at a first end, an outlet 464 at a second end, and a lumen defined by a tubular sidewall 463 of the drum-mounted fluid conduit 460 extending from the inlet 462 to the outlet 464. Although the inlet 462 and the outlet 464 are shown as being free (e.g., detached from the rotatable drum 475, the stationary frame 440, and the thermal ring), the inlet 462 may be fluidically coupled to the outlet of the thermal ring fluid conduit of the thermal ring and the outlet 464 may be fluidically coupled to the inlet of the thermal ring fluid conduit of the thermal ring such that fluid may flow between the thermal ring fluid conduit and the drum-mounted fluid conduit 460. For example, the thermal ring fluid conduit and the drum-mounted fluid conduit 460 may form at least a portion of a loop-shaped fluid flow path. The inlet 462 and the outlet 464 of the drum-mounted fluid conduit 460 may be coupled to an outlet and an inlet, respectively, of the thermal ring fluid conduit via, for example, an opening in the rotatable drum 475. The drum-mounted fluid conduit 460 may be coupled to the rotatable drum 475 in proximity to one or more heat-generating components (e.g., the heat-generating component 470).

As shown in FIG. 4, the drum-mounted fluid conduit 460 may be arranged such that a portion of the drum-mounted fluid conduit 460 is in contact with the rotatable drum 475 and a portion of the drum-mounted fluid conduit 460 is in contact with the heat-generating component 470 such that the drum-mounted fluid conduit 460 thermally connects the rotatable drum 475 and the heat-generating component 470 with the thermal ring fluid conduit 252. Thus, heat generated by the heat-generating component 470 may be transferred to fluid within the drum-mounted fluid conduit 460 which may then flow to the thermal ring fluid conduit and the heat transferred to the thermal ring.

In some embodiments, the drum-mounted fluid conduit 460 may be arranged to improve contact between a sidewall of the drum-mounted fluid conduit 460 and a surface of the rotatable drum 475 and/or a surface of the heat-generating component 470. For example, a portion or segment of the drum-mounted fluid conduit 460 may be wrapped around the heat-generating component 470 (e.g., forming a spiral). In some embodiments, the drum-mounted fluid conduit 460 may include or be coupled to a conduit embedded within a heat-generating component 470. For example, a converter target may include or be coupled to copper conduits embedded in a structure of the converter target to improve cooling of the converter target compared to only disposing a conduit adjacent to the outside of the converter target. As another example, a portion of the drum-mounted fluid conduit 460 may include a copper conduit brazed to the structure of a linear accelerator. The drum-mounted fluid conduit 460 may be arranged in such a way as to maximize a contact area between the drum-mounted fluid conduit 460 and the heat generating component 470 to improve heat transfer efficiency. As another example, although FIG. 4 shows portions of the drum-mounted fluid conduit 460 extending across windows or fenestrations (e.g., fenestration 477) in the rotatable drum 475, in some embodiments the drum-mounted fluid conduit 460 may be attached to the rotatable drum 475 such that the drum-mounted fluid conduit 460 does not extend across windows or fenestrations and instead contacts the surface of the rotatable drum 475 and extends along the sides of the windows or fenestrations.

Figure 5A:
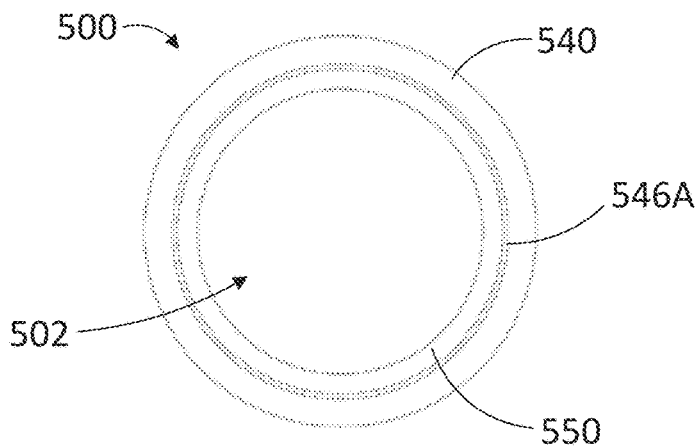
FIGS. 5A-5C are illustrative depictions of a temperature management system, according to an embodiment.
Figure 5B:
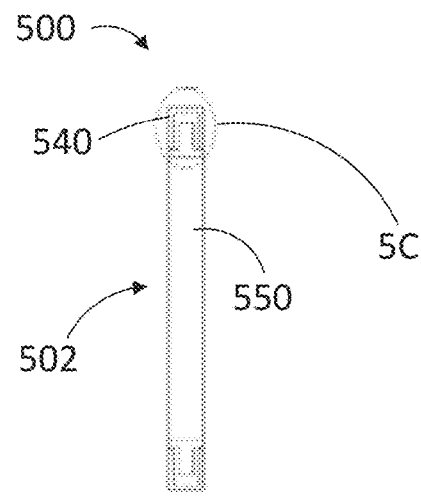

FIGS. 5A and 5B are a front view and a cross-sectional view, respectively, of a temperature management system 500. The temperature management system 500 may be used with any of the radiation therapy systems described herein, such as, for example, the radiation therapy system shown and described with respect to FIGS. 1A-1C. The system 500 may be similar in structure and/or function to any of the temperature management systems described herein, such as, for example, the system 200. The system 500 includes a stationary frame 540 and a thermal ring 550. The thermal ring 550 is coupled to the stationary frame 540 via a dynamic seal 546, and the stationary frame 540 and the thermal ring 550 are each ring-shaped such that the system 500 defines an opening 502.

Figure 5C:
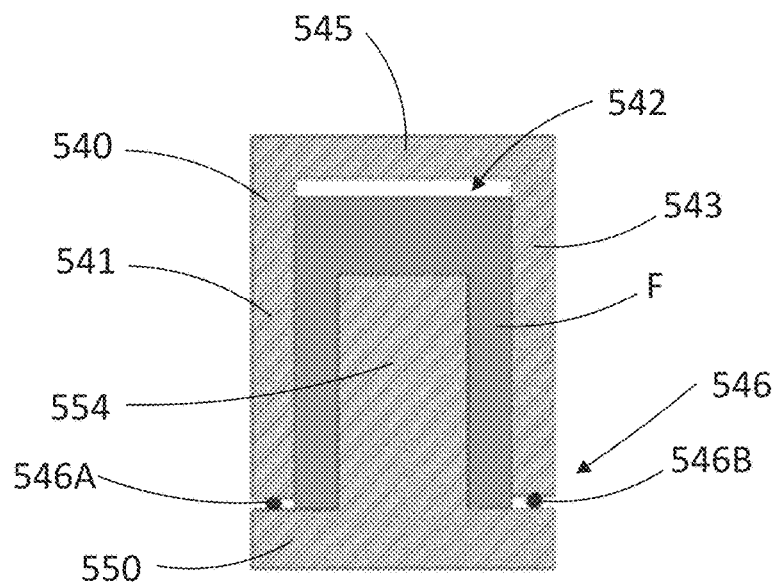

As shown in FIG. 5C, which is a close-up view of the cross-sectional portion identified as 5C in FIG. 5B, the thermal ring 550 is disposed relative to the stationary frame 540 such that the thermal ring 550 and the stationary frame 540 define an enclosure 542. The enclosure 542 may correspond to the shape of the stationary frame 540 (e.g., may be ring-shaped). The stationary frame 540 includes an outer wall 545, a first sidewall 541, and a second sidewall 543. The first sidewall 541 and the second sidewall 543 may project from the outer wall 545 such that the first sidewall 541, the second sidewall 543, the outer wall 545, and the thermal ring 550 collectively define the enclosure 542.

The thermal ring 550 includes a projecting portion 554 (also referred to as a "fin"). The projecting portion 554 may extend into the enclosure 542 and/or partially define the enclosure 542. As shown, the projecting portion 554 is shaped as a ring having a rectangular cross-section. The projecting portion 554, however, may have an suitable shape. For example, the projecting portion 554 may be shaped as a ring having a triangular cross-section or a rounded cross-section.

As described above, the thermal ring 550 is coupled to the stationary frame 540 via the dynamic seal 546. As shown in FIG. 5C, the dynamic seal 546 may include a first seal portion 546A and a second seal portion 546B. The first seal portion 546A is disposed between the first sidewall 541 and the thermal ring 550 and the second seal portion 546B is disposed between the second sidewall 543 and the thermal ring 550 such that fluid F disposed within the enclosure 542 is maintained within the enclosure 542. The fluid F disposed within the enclosure 542 may form a loop. In some embodiments, the fluid F is water. The fluid F may have a neutral pressure within the enclosure 542. The first seal portion 546A and the second seal portion 546B may be ring-shaped such that each of the first seal portion 546A and the second seal portion 546B correspond to the shape of the interface or gap between the thermal ring 550 and the stationary frame 540. The first seal portion 546A and the second seal portion 546B are each dynamic and thus configured to maintain a seal between the thermal ring 550 and the stationary frame 540 during rotary motion of the thermal ring 550 relative to the stationary frame 540. In some embodiments, the thermal ring 550 may rotate at, for example, 60 RPM relative to the stationary frame 540.

The thermal ring 550 may be coupled to a rotatable drum of a radiation therapy system, such as a rotatable drum of any of the radiation therapy systems described herein. The rotatable drum may be, for example, a rotatable gantry, such as any of the rotatable gantries described herein. The rotatable drum may be configured to rotate relative to the stationary frame 540. The thermal ring 550 may be coupled to the rotatable drum via any suitable method such that rotation of the rotatable drum causes corresponding rotation of the thermal ring 550. The thermal ring 550 may be mounted to the rotatable drum such that a bore of the rotatable drum is aligned with the opening of the thermal ring 550 and the stationary frame 540 (e.g., such that the bore of the rotatable drum and the opening of the thermal ring 550 are coaxial). A heat-generating component, such as any of the heat-generating components described herein, may be disposed on the rotatable drum such that the heat-generating component and the thermal ring 550 are coupled via the rotatable drum. The thermal ring 550 includes a thermally-conductive substrate configured to be in thermal contact with the heat-generating component such that heat from a heat-generating component may be transferred to the stationary frame 540 from the thermal ring 550 via the fluid F in the enclosure 542.

The system 500 may include or be coupled to a number of fluid conduits (not shown). The fluid conduits may be the same or similar in structure and/or function to any of the drum-mounted fluid conduits described herein (e.g., the drum-mounted fluid conduit 260). For example, each fluid conduit may include a sidewall that defines a lumen. Each fluid conduit may form a loop. For example, each fluid conduit may have a first end and a second end, and the first end may be coupled to the second end such that fluid may flow in a continuous loop through the fluid conduit. Each fluid conduit may be arranged such that at least a portion of each fluid conduit is in contact with a rotatable drum and/or a heat-generating component (such as any of the rotatable drums and/or heat-generating components described herein) such that the fluid conduit thermally connects the rotatable drum and/or the heat-generating component with the thermal ring 550. Thus, heat generated by the heat-generating component may be transferred to the thermal ring 550 via a fluid transferrable between a portion of a fluid conduit positioned proximate or adjacent the heat-generating component and a portion of the fluid conduit position proximate or adjacent the thermal ring 550.

In some embodiments, the stationary frame 540 may include a heat exchanger (not shown). The heat exchanger may be in thermal and/or fluid communication with the enclosure 542 and may be configured to cool the fluid F within the enclosure 542. The heat exchanger may be configured to maintain the fluid F within the enclosure 542 at a temperature below the temperature of the projecting portion 554 and/or a remainder of the thermal ring 550 such that thermal energy may be drawn from the projecting portion 554 and/or a remainder of the thermal ring 550 into the fluid F, cooling the projecting portion 554 and/or a remainder of the thermal ring 550. In some embodiments, the fluid F within the enclosure 542 may be cool city water that is exchanged after being heated and/or continuously via, for example, a fluid pump. In some embodiments, thermal energy may alternatively or additionally be transferred from the fluid F to the stationary frame 540. Thermal energy may also be transferred from the stationary frame 540 and into the surrounding environment when the temperature of the surrounding environment is below the temperature of the stationary frame 540.

In some embodiments, the system 500 may also include one or more sensors (not shown) configured to detect liquid fluid (e.g., water). The sensors may be disposed relative to the stationary frame 540 and the thermal ring 550 such that the sensors may detect if liquid fluid leaks from the enclosure 542 beyond the dynamic seal 546. The one or more sensors may be configured such that an audible and/or visual indicator may be provided to a user if the one or more sensors senses the presence of liquid fluid. If a user receives an audible and/or visual indication that fluid is leaking from the enclosure 542, the user may discontinue use of the system 500.

In use, heat generated by a heat-generating component on a rotatable drum to which the thermal ring 550 is mounted may be transferred to a fluid circulated through a fluid conduit (such as any of the drum-mounted fluid conduits described herein) via a sidewall of the fluid conduit such that the temperature of the fluid increases. The warmed fluid may then flow through the fluid conduit to a portion of the fluid conduit adjacent the thermal ring 550. As the warmed fluid is circulated toward the thermal ring 550, cooler fluid within the fluid conduit may simultaneously flow into a portion of the fluid conduit near or adjacent the heat-generating component. As the fluid is circulated through the portion of the fluid conduit adjacent the thermal ring 550, thermal energy may transfer from the fluid within the fluid conduit, through a sidewall of the fluid conduit, and into the thermal ring 550 such that the temperature of the fluid within the fluid conduit is reduced. The heat transferred to the thermal ring 550 may then be transferred to the projecting portion 554, and then transferred from the projecting portion 554 to the fluid F disposed within the enclosure 542. In some embodiments, the heated fluid within the enclosure 542 may be exchanged for cooler city water via a fluid pump.

Figure 6A:
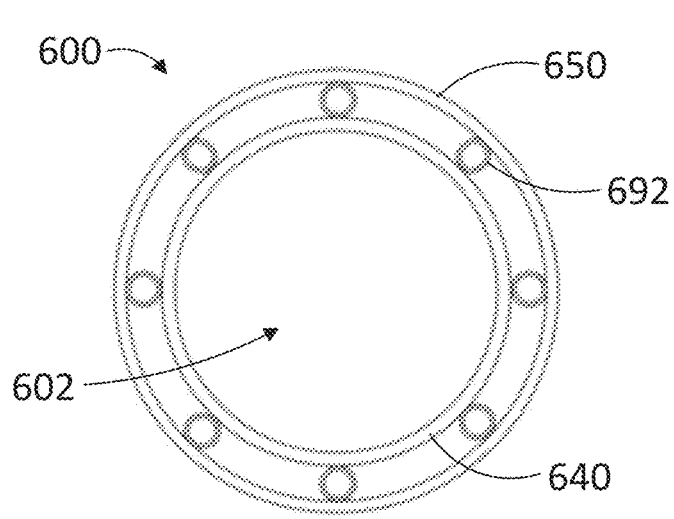
FIGS. 6A-6C are illustrative depictions of a temperature management system, according to an embodiment.
Figure 6B:
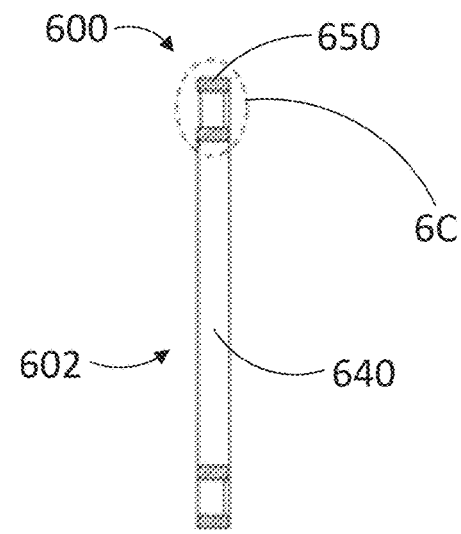

FIGS. 6A and 6B are a front view and a cross-sectional view, respectively, of a temperature management system 600. The temperature management system 600 may be used with any of the radiation therapy systems described herein, such as, for example, the radiation therapy system shown and described with respect to FIGS. 1A-1C. The system 600 may be similar in structure and/or function to any of the temperature management systems described herein, such as, for example, the system 200. The system 600 includes a stationary frame 640 and a thermal ring 650. The thermal ring 650 is coupled to the stationary frame 640 via a number of roll rings 692, and the stationary frame 640 and the thermal ring 650 are each ring-shaped such that the system 600 defines an opening 602.

Figure 6C:
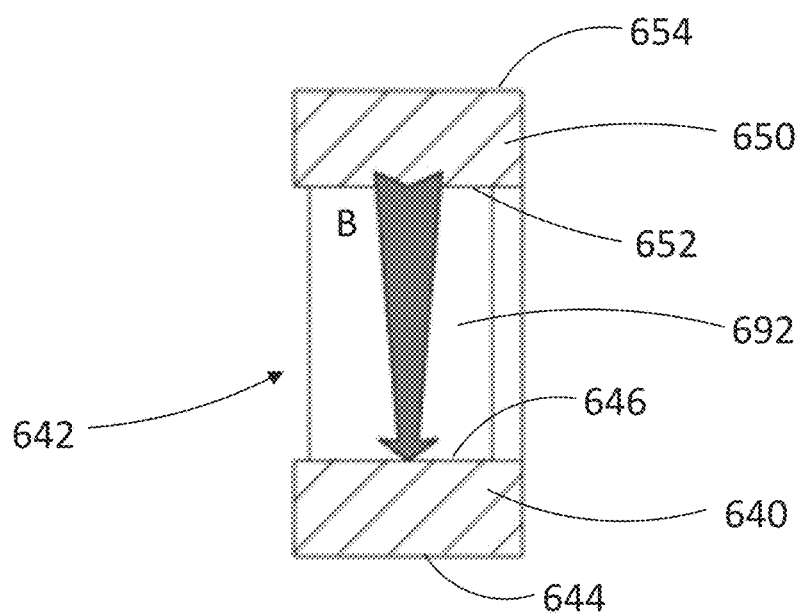

As shown in FIG. 6C, which is a close-up view of the cross-sectional portion identified as 6C in FIG. 6B, the thermal ring 650 is disposed relative to the stationary frame 640 such a ring-shaped space 642 is defined between the thermal ring 650 and the stationary frame 640. The stationary frame 640 includes an inner surface 644 and an outer surface 646. The thermal ring 650 includes an inner surface 652 and an outer surface 654. The roll rings 692 are disposed in the ring-shaped space 642 such that a first portion of each roll ring 692 contacts the outer surface 644 of the stationary frame 640 and a second portion of each roll ring 692 contacts the inner surface 652 of the thermal ring 650. Each roll ring 692 may be formed of and/or include any suitable thermally conductive substrate such that thermal energy may be transferred between the thermal ring 650 and the stationary frame 640 via the number of roll rings 692 via conduction. Although the system 600 is shown as including eight roll rings 692, in some embodiments the system 600 may include any suitable number of roll rings 692.

The thermal ring 650 may be coupled to a rotatable drum of a radiation therapy system, such as a rotatable drum of any of the radiation therapy systems described herein. The rotatable drum may be, for example, a rotatable gantry, such as any of the rotatable gantries described herein. The rotatable drum may be configured to rotate relative to the stationary frame 640. The thermal ring 650 may be coupled to the rotatable drum via any suitable method such that rotation of the rotatable drum causes corresponding rotation of the thermal ring 650. The thermal ring 650 may be mounted to the rotatable drum such that a bore of the rotatable drum is aligned with the opening of the thermal ring 650 and the stationary frame 640 (e.g., such that the bore of the rotatable drum and the opening of the thermal ring 650 are coaxial). A heat-generating component, such as any of the heat-generating components described herein, may be disposed on the rotatable drum such that the heat-generating component and the thermal ring 650 are coupled via the rotatable drum. The thermal ring 650 includes a thermally-conductive substrate configured to be in thermal contact with the heat-generating component such that heat from a heat-generating component may be transferred via conduction to the stationary frame 640 from the thermal ring 650 via the roll rings 692.

The thermal ring 650 is configured to rotate relative to the stationary frame 640. In some embodiments, the thermal ring 650 may rotate at, for example, 60 RPM. As the thermal ring 650 rotates (e.g., with the rotatable drum), the roll rings 692 may also rotate. For example, the roll rings 692 may rotate in the opposite direction to the thermal ring 650 (e.g., due to friction with the inner surface 652) along the outer surface 646 of the stationary frame 640. Portions of the roll rings 692 near the thermal ring 650 may be warmer than portions of the roll rings 692 near the stationary frame 640. A portion of the roll ring 692 may receive thermal energy from the thermal ring 650, and then roll from a position contacting the inner surface 652 of the thermal ring 650 to a position contacting the outer surface 646 of the stationary frame 640 such that, as the roll rings 692 rotate along the inner surface 652 of the thermal ring 650 and the outer surface 646 of the stationary frame 640, thermal energy may be conducted from the thermal ring 650, to a roll ring 692, and to the stationary frame 640.

The system 600 may include or be coupled to a number of fluid conduits (not shown). The fluid conduits may be the same or similar in structure and/or function to any of the drum-mounted fluid conduits described herein (e.g., the drum-mounted fluid conduit 260). For example, each fluid conduit may include a sidewall that defines a lumen. Each fluid conduit may form a loop. For example, each fluid conduit may have a first end and a second end, and the first end may be coupled to the second end such that fluid may flow in a continuous loop through the fluid conduit. Each fluid conduit may be arranged such that at least a portion of each fluid conduit is in contact with a rotatable drum and/or a heat-generating component (such as any of the rotatable drums and/or heat-generating components described herein) such that the fluid conduit thermally connects the rotatable drum and/or the heat-generating component with the thermal ring 650. Thus, heat generated by the heat-generating component may be transferred to the thermal ring 650 via a fluid transferrable between a portion of a fluid conduit positioned proximate or adjacent the heat-generating component and a portion of the fluid conduit position proximate or adjacent the thermal ring 650.

In some embodiments, the system 600 may include one or more fluid conduits disposed proximate or adjacent the inner surface 644 of the stationary frame 640 such that thermal energy that has been transferred to the stationary frame 640 via the roll rings 692 may be transferred to fluid within the one or more fluid conduits and may flow away from the stationary frame 640. For example, the one or more fluid conduits disposed proximate or adjacent the inner surface 644 of the stationary frame 640 may include a sidewall defining a lumen. Each conduit of the one or more fluid conduits may be fluidically coupled to a source of water (e.g., chilled city water). The source of water may provide fluid at a temperature below the temperature of the stationary frame 640 such that the fluid may draw heat from the stationary frame, through the sidewall of the one or more fluid conduits, and into the fluid. The fluid may then flow away from the stationary frame 650 to, for example, a drain.

In use, heat generated by a heat-generating component on a rotatable drum to which the thermal ring 650 is mounted may be transferred to a fluid circulated through a fluid conduit (such as any of the drum-mounted fluid conduits described herein) via a sidewall of the fluid conduit such that the temperature of the fluid increases. The warmed fluid may then flow through the fluid conduit to a portion of the fluid conduit adjacent the thermal ring 650. As the warmed fluid is circulated toward the thermal ring 650, cooler fluid within the fluid conduit may simultaneously flow into a portion of the fluid conduit near or adjacent the heat-generating component. As the fluid is circulated through the portion of the fluid conduit adjacent the thermal ring 650, thermal energy may transfer from the fluid within the fluid conduit, through a sidewall of the fluid conduit, and into the thermal ring 650 such that the temperature of the fluid within the fluid conduit is reduced. The heat transferred to the thermal ring 650 may then be transferred via conduction to the roll rings 692, and then transferred from the roll rings 692 to the stationary frame 640. In some embodiments, thermal energy may then be drawn from the stationary frame 640 to fluid within one or more fluid conduits disposed proximate or adjacent the inner surface 644 of the stationary frame 640. The fluid may then flow from the system 600 via, for example, a drain.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein may include various combinations and/or sub-combinations of the functions, components, and/or features of the different embodiments described.

The invention claimed is:

1. An apparatus, comprising:
    a stationary frame;
    a rotatable drum rotatably coupled to the stationary frame;
    a thermal ring coupled to the rotatable drum between the rotatable drum and the stationary frame such that the thermal ring and the stationary frame define an enclosure, wherein the thermal ring includes a thermally-conductive substrate configured to be in thermal contact with a heat-generating component; and
    wherein heat from the heat-generating component is transferred to the stationary frame via the enclosure.

2. The apparatus of claim 1, the thermal ring further comprising a fluid conduit having a sidewall that defines a lumen, wherein at least a portion of the sidewall is in thermal contact with the thermally-conductive substrate.

3. The apparatus of claim 2, wherein the fluid conduit is at least partially embedded in the thermally-conductive substrate.

4. The apparatus of claim 2, wherein the fluid conduit is located within the thermally-conductive substrate.

5. The apparatus of claim 2, wherein the thermal ring has a circumference and the fluid conduit extends along at least a portion of the circumference.

6. The apparatus of claim 5, wherein the fluid conduit is at least partially ring-shaped.

7. The apparatus of claim 2, wherein the fluid conduit sidewall includes a metal.

8. The apparatus of claim 2, wherein the fluid conduit is a first fluid conduit, and wherein the heat-generating component is attached to the rotatable drum and a second fluid conduit that thermally connects the heat-generating component with the fluid conduit.

9. The apparatus of claim 8, wherein the first fluid conduit and the second fluid conduit are in fluid communication such that heat generated by the heat-generating component is transferred to the first fluid conduit via a fluid within the first and second fluid conduits.

10. The apparatus of claim 8, further comprising a fluid pump coupled to at least one of the first fluid conduit or the second fluid conduit, the fluid pump configured to circulate fluid between the first fluid conduit and the second fluid conduit.

11. The apparatus of claim 1, wherein the stationary frame is ring-shaped.

12. The apparatus of claim 1, wherein the stationary frame includes a stationary ring, the stationary ring and the thermal ring being coaxially disposed.

13. The apparatus of claim 1, wherein the heat-generating component is a therapeutic radiation source.

14. The apparatus of claim 1, wherein the stationary frame includes a heat exchanger in thermal communication with the enclosure, the heat exchanger configured to deliver air to the enclosure.

15. The apparatus of claim 1, further comprising a plurality of thermally-conductive extending members coupled to the thermally-conductive substrate and extending into the enclosure.

16. The apparatus of claim 15, wherein each extending member of the plurality of extending members is cylindrically-shaped.

17. The apparatus of claim 15, wherein each extending member of the plurality of extending members is shaped as a rectangular prism.

18. The apparatus of claim 15, wherein the plurality of extending members includes at least one hundred extending members.

* * * * *